US012568963B2

(12) United States Patent
Coats et al.

(10) Patent No.: US 12,568,963 B2
(45) Date of Patent: Mar. 10, 2026

(54) COMPOUNDS AND COMPOSITIONS FOR NEMATODE TREATMENT

(71) Applicant: IOWA STATE UNIVERSITY RESEARCH FOUNDATION, INC., Ames, IA (US)

(72) Inventors: Joel Robert Coats, Ames, IA (US); James Scott Klimavicz, Ames, IA (US); Jefferson De Oliveira Barizon, Ames, IA (US); Gregory Lee Tylka, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 0 days.

(21) Appl. No.: 18/492,874

(22) Filed: Oct. 24, 2023

(65) Prior Publication Data

US 2024/0065264 A1 Feb. 29, 2024

Related U.S. Application Data

(62) Division of application No. 17/181,873, filed on Feb. 22, 2021, now Pat. No. 11,832,613.

(60) Provisional application No. 62/979,921, filed on Feb. 21, 2020.

(51) Int. Cl.

| | |
|---|---|
| ***A01N 31/04*** | (2006.01) |
| ***A01N 31/14*** | (2006.01) |
| ***A01N 37/42*** | (2006.01) |
| ***A01N 43/84*** | (2006.01) |
| ***C07C 49/235*** | (2006.01) |
| ***C07C 49/255*** | (2006.01) |
| ***C07C 69/757*** | (2006.01) |
| ***C07C 323/22*** | (2006.01) |
| ***C07D 295/112*** | (2006.01) |

(52) U.S. Cl.

CPC ............ *A01N 31/04* (2013.01); *A01N 31/14* (2013.01); *A01N 37/42* (2013.01); *A01N 43/84* (2013.01); *C07C 49/235* (2013.01); *C07C 49/255* (2013.01); *C07C 69/757* (2013.01); *C07C 323/22* (2013.01); *C07D 295/112* (2013.01)

(58) Field of Classification Search

CPC ...................................................... A01N 31/04

See application file for complete search history.

(56) References Cited

U.S. PATENT DOCUMENTS

| | | | | |
|---|---|---|---|---|
| 2,335,384 | A | 11/1943 | Bousquet et al. | |
| 3,112,346 | A | 11/1963 | Weil et al. | |
| 3,917,718 | A * | 11/1975 | Collins | C07C 49/235 568/313 |
| 4,005,103 | A * | 1/1977 | Teulon | C07D 317/54 568/313 |
| 4,275,201 | A * | 6/1981 | Collins | C07C 37/055 564/305 |
| 8,642,660 | B2 * | 2/2014 | Goldfarb | A61K 31/122 514/18.9 |
| 2008/0300318 | A1 | 12/2008 | Wang et al. | |

FOREIGN PATENT DOCUMENTS

| | | | |
|---|---|---|---|
| EP | 2150108 | A1 | 2/2010 |
| FR | 1366363 | | 7/1964 |
| JP | 2001278702 | | 10/2001 |

OTHER PUBLICATIONS

Yang, Youji Huaxue (2016), 36(5), 1073-1079.*

Barizon, Jefferson O., "Synthetic Derivatives of Plants Essential Oils as Possible Nematicides" ATRB: Oral Departmental Presentation, Feb. 22, 2019.

Barizon et al., "Analogs of Plant Essential Oils as Possible Nematicides" poster presentation at Annual Society of Nematologists in Raleigh, NC., Jul. 6, 2019.

Cornell et al., "Comparisons of Halogenated β-Nitrostyrenes as Antimicrobial Agents," Appl. Sci. 4:380-389 (2014).

Caboni et al., "Potent Nematicidal Activity of Phthalaldehyde, Salicylaldehyde, Cinnamic Aldehyde Against Meloidogyne Incognita" J. Agric. Food Chem. 6161:1794-1803 (2013).

Garbow and Gaede, "A New Method for the Analysis of Granular Pesticide Formulations," Journal of Agricultural and Food Chemistry 38(4):996-9 (1990).

Venkatesh et al., "Role of the Development Scientist in Compound Lead Selection and Optimization," J. Pharm. Sci. 89:145-154 (2000).

J. G. Cannon, Chapter Nineteen in Burger's Medicinal Chemistry and Drug Discovery, Fifth Edition, vol. I: Principles and Practice, Wiley-Interscience 1995, pp. 783-802, 784.

West (West, Solid State Chemistry and Its Applications, John Wiley & Sons, 1984).

* cited by examiner

*Primary Examiner* — Nizal S Chandrakumar

(74) *Attorney, Agent, or Firm* — Troutman Pepper Locke LLP (Rochester)

(57) ABSTRACT

Disclosed herein are compounds and compositions for nematode treatment. In particular, disclosed are compounds of formula (I), a method of treating a plant or a growing media for a nematode with compounds of formula (II), compositions, and methods of use.

2 Claims, 10 Drawing Sheets

COMPOUNDS AND COMPOSITIONS FOR NEMATODE TREATMENT

This application is a divisional of U.S. patent application Ser. No. 17/181,873, filed Feb. 22, 2021, which claims priority benefit of U.S. Provisional Patent Application Ser. No. 62/979,921, filed Feb. 21, 2020, which are hereby incorporated by reference in their entirety.

FIELD

The present application relates to compounds and compositions for nematode treatment, and to methods of treating a plant or a growing media for a nematode using compounds described herein.

BACKGROUND

Plant-parasitic nematodes are responsible for tremendous agricultural damage each year, with economic loss estimates in the tens of billions of dollars worldwide. For example, the soybean cyst nematode is a pest of soybeans, and is responsible for the loss of approximately 617 million bushels of soybeans over the five-year period of 2010 to 2014. Other plant-parasitic nematodes, including the root-knot (Meloidogyne spp.) and root-lesion (Pratylenchus spp.) nematodes are economically relevant pests, feeding on high-value crops including peppers, tomatoes, potatoes, and many other fruits and vegetables. The soybean cyst nematode ("SCN"), Heterodera glycines, is the most damaging pest of soybean in North America, and root-knot nematodes ("RKN"), Meloidogyne spp., are widely distributed in agricultural fields worldwide and cause disease in a vast range of plant species.

Management of harmful nematodes relies on use of multiple strategies such as growing nematode-resistant varieties, alternating crop cycles with non-host crops, and using biological and chemical controls. Many of the traditional pesticides to kill nematodes are soil sterilants, killing nearly everything in the soil or growing media. As such, most of these compounds are highly toxic to humans and other animals. Moreover, methyl bromide, which was until recently used as a cheap and effective growing media sterilant, was banned under the Montreal Protocol, as it is a strong ozone depleting substance. Other growing media sterilants are less effective or more expensive.

Several pesticides have been targeted specifically toward plant-parasitic nematodes. However, many of these compounds, such as the carbamate aldicarb, are extremely toxic to mammals. Other compounds with lower off-target toxicity have been developed and marketed, though the efficacy of some of these compounds remains in question.

There are no nematode-resistant varieties for many cultivated crops, and the effectiveness of existing resistance is eroding in some cases. In addition, economically marketable non-host crops are not available in certain regions where Meloidogyne is prevalent. These constraints combined with the declining role of chemical control demonstrate that new nematode management strategies are needed.

Plants produce a variety of secondary plant metabolites, many of which are synthesized by plants to protect from plant parasites, pathogens, or insect/animal herbivory. These compounds may therefore serve as starting points for the development of new compounds that may possess desirable biological activities against plant pests.

The present application is directed to overcoming these and other deficiencies in the art.

SUMMARY

One aspect of the present application relates to a compound of formula (I) having the following structure:

(I)

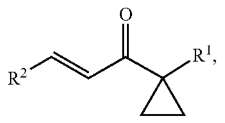

or a stereoisomer, salt, oxide, or solvate thereof, where $R^1$ is H or

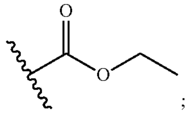 [SMILES: *C(=O)OCC]

;

and $R^2$ is

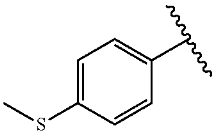

,

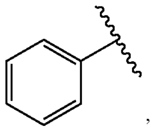

,

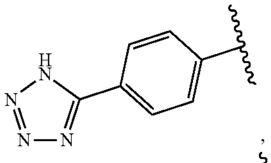

,

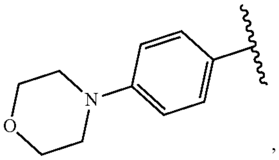

,

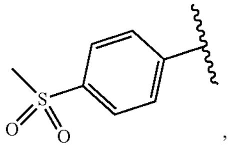

,

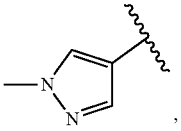

,

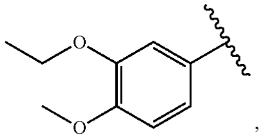

,

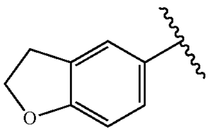

,

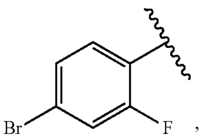

, or

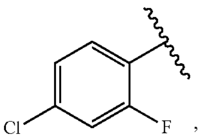

, where

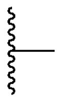

is an attachment site; with the proviso that when $R^1$ is H, $R^2$ is not phenyl.

Another aspect of the present application relates to a method of treating a plant or a growing media for a nematode. This method involves contacting a plant or a growing media with a compound of formula (II) having the following structure:

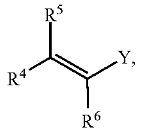

(II)

or a stereoisomer, salt, oxide, or solvate thereof, where

Y is

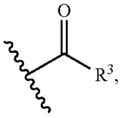
,
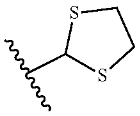
,
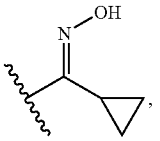
, or $NO_2$;

$R^3$ is methyl, cyclopropyl, isopropyl, tert-butyl, $C_1$-$C_3$ alkoxy, or

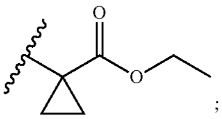 [SMILES: *C1(C(=O)OCC)CC1]
;

$R^4$ is selected from the group consisting of:

phenyl;

phenyl substituted only at the para position with a halogen, $CF_3$, $NO_2$, $S(C_1$-$C_3$ alkyl), CN, dimethylamine, $C_1$-$C_3$ alkyl, sulfonyl, $C_1$-$C_3$ alkoxy, morpholinyl, or tetrazolyl;

phenyl substituted only at the meta position with a halogen;

phenyl substituted only at the para and meta positions with substituents independently selected from halogen and $C_1$-$C_3$ alkoxy;

phenyl substituted only at the para and ortho positions with a halogen;

$C_1$-$C_3$ alkyl substituted pyrazolyl;

2,3-dihydrobenzofuranyl;

pyridinyl;

thiophenyl; and benzodioxolyl;

$R^5$ is H or CN; and $R^6$ is H or Me to treat the plant or growing media for the nematode.

A further aspect of the present application relates to a composition comprising:

a compound of formula (II) having the following structure:

(II)

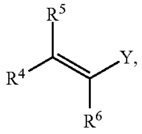

or a stereoisomer, salt, oxide, or solvate thereof, where

Y is

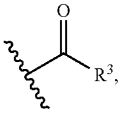
,
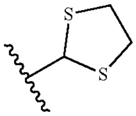
,
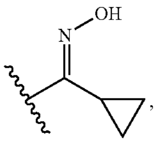
, or $NO_2$;

$R^3$ is methyl, cyclopropyl, isopropyl, tert-butyl, $C_1$-$C_3$ alkoxy, or

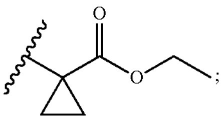 [SMILES: *C1(C(=O)OCC)CC1]
;

$R^4$ is selected from the group consisting of:

phenyl;

phenyl substituted only at the para position with a halogen, $CF_3$, $NO_2$, $S(C_1$-$C_3$ alkyl), CN, dimethylamine, $C_1$-$C_3$ alkyl, sulfonyl, $C_1$-$C_3$ alkoxy, morpholinyl, or tetrazolyl;

phenyl substituted only at the meta position with a halogen;

phenyl substituted only at the para and meta positions with substituents independently selected from halogen and $C_1$-$C_3$ alkoxy;

phenyl substituted only at the para and ortho positions with a halogen;

$C_1$-$C_3$ alkyl substituted pyrazolyl;

2,3-dihydrobenzofuranyl;

pyridinyl;

thiophenyl; and benzodioxolyl; and $R^5$ is H or CN;

$R^6$ is H or Me; and an agriculturally acceptable carrier.

Another aspect of the present application relates to a method of treating a plant or a growing media for a nematode. This method involves contacting a plant or a growing media with a compound having a structure

JSK1132

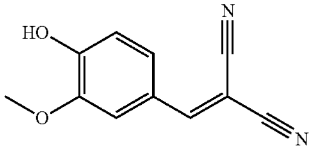

to treat the plant or growing media for a nematode.

The present application describes the synthesis of derivatives and analogs of natural terpenes for nematicidal use, and provides experimental data showing the activity and effectiveness of such compounds.

The synthesis program described herein examined compounds having a structure related to naturally-occurring compounds. Close derivatives and analogs, as well as more distant derivatives and analogs, were all tested first in a simple bioassay on SCN, on egg hatch to $2^{nd}$ stage juveniles. Subsequent testing included a bioassay with root knot nematode ("RKN") and with cucumber seedlings in sand, and SCN in greenhouse pot-testing in soil. Later, the more efficacious compounds were tested against RKN.

The compounds were primarily designed to be steric analogs (including isosteres) and/or electronically comparable to naturally-occurring molecules. Initial testing was on simply-substituted cinnamaldehydes (e.g., 4-chlorocinnamaldehyde and α-chlorocinnamaldehyde). Other variations included substituted styrenes, and related families of molecules.

Using this strategy, a panel of natural monoterpenoids and phenylpropanoids was first screened, many of which have been shown to possess insecticidal or insect-repellent properties previously. Initial screening was performed by dissolving the tested compounds in water and a small amount of solvent, and then determining the level of hatch inhibition of nematode eggs as compared to a solvent control.

Identified herein are compounds with improved biological activity against nematodes, and increased stability with respect to photodegradation and soil degradation.

As shown in the examples infra, the effects of several synthetic analogs of monoterpenes from plant essential oils were tested on the hatching of SCN in vitro and on galling of cucumber roots caused by RKN in vivo.

BRIEF DESCRIPTION OF THE DRAWINGS

FIG. 2A shows a 12-day-old cucumber plant at the time of treatment application and addition of nematode eggs. FIG. 2B shows cone-tainers with soil treated, ready for nematode infestation. FIG. 2C shows galling of cucumber roots caused by root-knot nematode in water control treatment 15 days after addition of nematode eggs.

FIG. 3A is a graph showing the effects of synthetic analogs of monoterpenes on SCN hatching after 15 days based on continuous exposure at 100 ppm. FIG. 3B is a graph showing the effects of synthetic analogs of monoterpenes on SCN hatching after 15 days based on continuous exposure at 10 ppm. FIG. 3C is a graph showing the effects of synthetic analogs of monoterpenes on SCN hatching after 15 days based on short-term exposure at 100 ppm. FIG. 3D is a graph showing the effects of synthetic analogs of monoterpenes on SCN hatching after 15 days based on short-term exposure at 10 ppm. Only treatments that were significantly different (alpha=0.05) from the solvent control are shown in the graphs of FIGS. 3A-D.

FIG. 5A is a photograph showing SCN-infested soil spread in a band through the middle of the microplot and incorporated into the soil. FIG. 5B is a photograph of hand planting of seeds in a furrow created manually over the SCN-infested, treated soil. FIG. 5C is a photograph of seedling emergence 8 days after planting ("DAP"). FIG. 5D is a photograph showing seedlings 14 DAP. FIG. 5E is a photograph showing the plants 52 DAP. FIG. 5F is an aerial photograph of the entire experimental plot 57 DAP. FIG. 5G is a photograph of the plants 74 DAP. FIG. 5H is a photograph showing the mature plants 124 DAP.

DETAILED DESCRIPTION

Figure 1A:
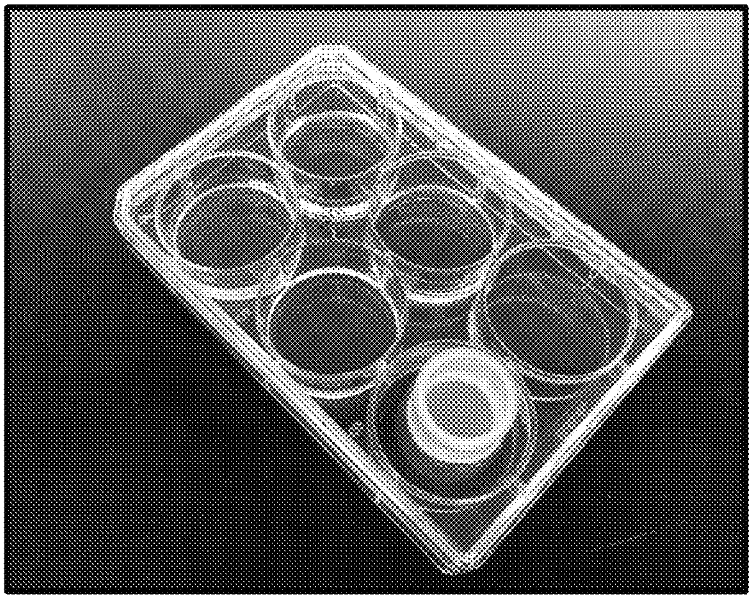
FIGS. 1A-B are photographs showing a six-well plate containing a hatching unit (FIG. 1A) and SCN egg and hatched second-stage juvenile (FIG. 1B).

Disclosed herein are compounds and compositions for nematode treatment and methods of treating a plant or a growing media for a nematode using compounds described herein. In particular, newly synthesized and biorationally designed compounds described herein are shown to be useful against nematodes or for controlling nematodes in a growing media.

One aspect of the present application relates to a compound of formula (I) having the following structure:

(I)

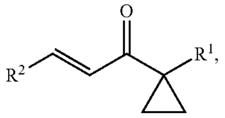

or a stereoisomer, salt, oxide, or solvate thereof, where $R^1$ is H or

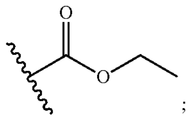 [SMILES: *C(=O)OCC]
;

and $R^2$ is

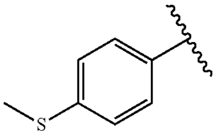
,
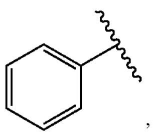
,
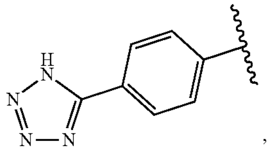
,
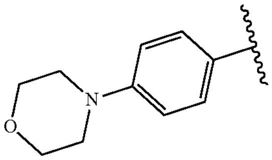
,
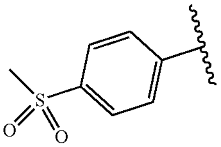
,
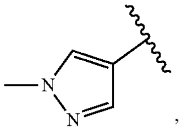
,

-continued

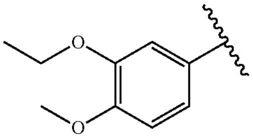, 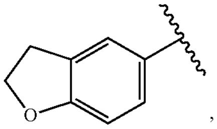,

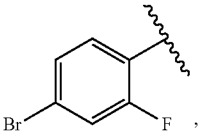, or 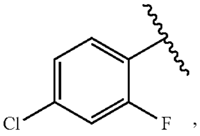, where

is an attachment site;

with the proviso that when $R^1$ is H, $R^2$ is not phenyl.

As used herein, the term "compound" and equivalent expressions means compounds of formulae (I) and (II) as described herein. Also contemplated are salts, oxides, solvates, e.g., hydrates, and inclusion complexes of compounds of formulae (I) and (II), where the context so permits, as well as any stereoisomeric form, or a mixture of any such forms of that compound in any ratio.

Inclusion complexes are described in Remington, *The Science and Practice of Pharmacy,* 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

Compounds described herein may contain one or more asymmetric centers and may thus give rise to enantiomers, diastereomers, and other stereoisomeric forms. Each chiral center may be defined in terms of absolute stereochemistry as (R)- or (S)-. The present application is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

In some embodiments, compounds of formula (I) described herein (and compounds of formula (II) described infra) are in a substantially pure form.

In some embodiments, compounds of formula (I) described herein (and compounds of formula (II) described infra) may be a single enantiomer or diastereomer or a racemic or diastereomeric mixture.

In some embodiments of the compound of formula (I), $R^1$ is H.

In some embodiments, in the compound of formula (I), $R^1$ is H and the compound has the following structure:

JSK3091

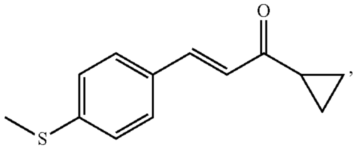,

JSK3142

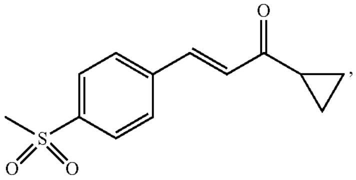,

JSK3169

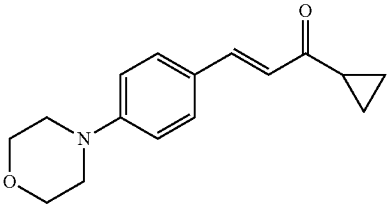,

JSK3209

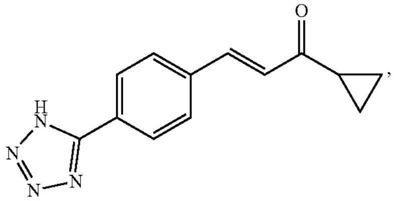,

JSK3294

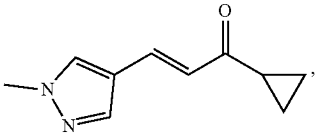,

JSK3296

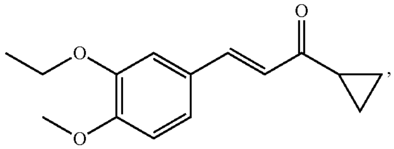,

JSK3297

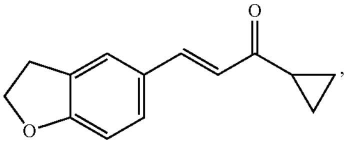,

JSK4018

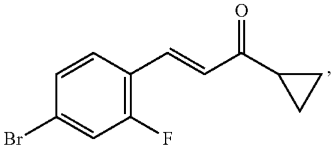, or

JSK4044

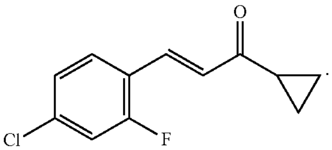.

In some embodiments of the compound of formula (I), $R^1$ is

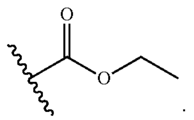 [SMILES: *C(=O)OCC]

In another embodiment, in the compound of formula (I) $R^1$ is

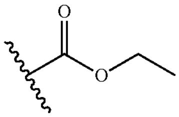 [SMILES: *C(=O)OCC]

and the compound has the following structure:

JSK3275

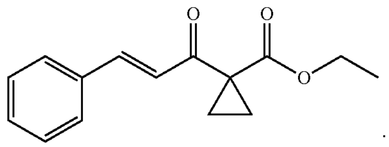

Compounds of formula (I) may be useful to protect plants against nematodes, especially nematodes harmful to plants, as described herein.

Compounds of formula (I) are encompassed by compounds of formula (II) described infra.

Another aspect of the present application relates to a method of treating a plant or a growing media for a nematode. This method involves contacting a plant or a growing media with a compound of formula (II) having the following structure:

(II)

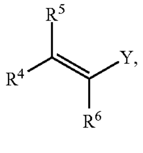

or a stereoisomer, salt, oxide, or solvate thereof, where

Y is

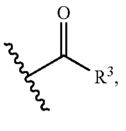 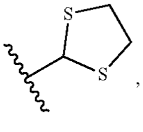, 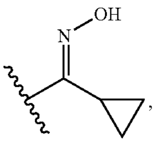, or $NO^2$;

$R^3$ is methyl, cyclopropyl, isopropyl, tert-butyl, $C_1$-$C_3$ alkoxy, or

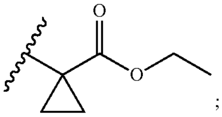 [SMILES: *C1(C(=O)OCC)CC1];

$R^4$ is selected from the group consisting of:
- phenyl;
- phenyl substituted only at the para position with a halogen, $CF_3$, $NO_2$, S($C_1$-$C_3$ alkyl), CN, dimethylamine, $C_1$-$C_3$ alkyl, sulfonyl, $C_1$-$C_3$ alkoxy, morpholinyl, or tetrazolyl;
- phenyl substituted only at the meta position with a halogen;
- phenyl substituted only at the para and meta positions with substituents independently selected from halogen and $C_1$-$C_3$ alkoxy;
- phenyl substituted only at the para and ortho positions with a halogen;
- $C_1$-$C_3$ alkyl substituted pyrazolyl;
- 2,3-dihydrobenzofuranyl;
- pyridinyl;
- thiophenyl; and
- benzodioxolyl;

$R^5$ is H or CN; and $R^6$ is H or Me to treat the plant or growing media for a nematode.

As used herein, the term "alkyl" means an aliphatic hydrocarbon group which may be straight or branched. The term "$C_1$-$C_3$ alkyl" means an alkyl of from 1 to 3 carbons. Exemplary "$C_1$-$C_3$ alkyl" groups include methyl, ethyl, n-propyl, and i-propyl.

The term "halogen" as used herein is intended to include any of fluorine, bromine, chlorine, and iodine.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents are described herein.

According to some embodiments, compounds of formulae (I) and (II) described herein, or substituents thereof, are substituted. By "substituted" it is meant that a group may have a substituent at a substitutable atom of the group (including more than one substituent on a single atom), provided that the designated atom's normal valency is not exceeded and the identity of each substituent is independent of the others. Combinations of substituents and/or variables are permissible only if such combinations result in stable compounds. By "stable compound" it is meant a compound that is sufficiently robust to survive isolation to a useful degree of purity from a reaction mixture, and formulation into an agent intended for a suitable use.

In some embodiments of the compounds disclosed herein, the compound is a compound of formula (II) where $R^4$ is phenyl substituted only at the para position with a halogen, $CF_3$, $NO_2$, S($C_1$-$C_3$ alkyl), CN, dimethylamine, $C_1$-$C_3$ alkyl, sulfonyl, $C_1$-$C_3$ alkoxy, morpholinyl, or tetrazolyl; phenyl substituted only at the meta position with a halogen; phenyl substituted at only the para and meta positions with substituents independently selected from halogen and $C_1$-$C_3$ alkoxy; phenyl substituted only at the para and ortho positions with a halogen; or $C_1$-$C_3$ alkyl substituted pyrazolyl.

According to this aspect of the present application, a plant or a growing media is treated with a compound of formula (II).

In some embodiments, a plant is treated with a compound of formula (II).

Suitable plants amenable to the treatment methods described herein include any plant vulnerable or susceptible to nematodes. A number of genera and species of nematodes are known to be highly damaging to a great number of plant hosts, including foliage plants, agronomic and vegetable crops, fruit and nut trees, turfgrass, and forest trees.

In some embodiments, a plant treated with a compound of formula (II) is a vegetable crop. In a particular embodiment, the plant is soybean (Glycine max).

Some of the most damaging nematodes to plants include, without limitation, root-knot (Meloidogyne spp.), cyst (Heterodera and Globodera spp.), root-lesion (Pratylenchus spp.), spiral (Hehcotylenchus spp.), burrowing (Radopholus similis), bulb and stem (Ditylenchus dipsaci), reniform (Rotylenchulus reniformis), dagger (Xiphinema spp.), bud and leaf (Aphelenchoides spp.), and Pine Wilt Disease (Bursaphelenchus xylophilus). According to the present application, any of these (or any other plant-parasitic nematode) may be treated according to the methods described herein.

In some embodiments, a growing media is treated with a compound of formula (II).

As used herein, the term "growing media" is meant to include soil or any other organic or inorganic material in which a plant may be grown or cultivated.

In carrying out methods described herein, a plant or a growing media is contacted with a compound of formula (II).

Contacting a plant or a growing media with a compound of formula (II) may involve contacting a plant or growing media with a compound of formula (II) or a composition disclosed herein, which composition contains a compound of formula (II).

In some embodiments of the compound of formula (II), Y is

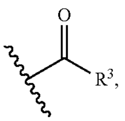

$R^3$ is cyclopropyl, and $R^5$ is H.

In some embodiments of the compound of formula (II), Y is

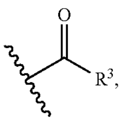

$R^3$ is cyclopropyl, $R^5$ is H, and $R^4$ is phenyl.

In some embodiments of the compound of formula (II), Y is

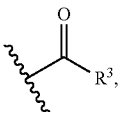

$R^3$ is cyclopropyl, $R^5$ is H, and $R^4$ is phenyl substituted only at the para position with a halogen, $CF_3$, $NO_2$, $S(C_1$-$C_3$ alkyl), CN, dimethylamine, $C_1$-$C_3$ alkyl, sulfonyl, $C_1$-$C_3$ alkoxy, morpholinyl, or tetrazolyl.

In some embodiments of the compound of formula (II), Y is

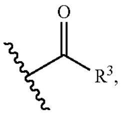

$R^3$ is cyclopropyl, $R^5$ is H, and $R^4$ is phenyl substituted only at the meta position with a halogen.

In some embodiments of the compound of formula (II), Y is

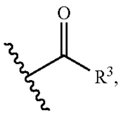

$R^3$ is cyclopropyl, $R^5$ is H, and $R^4$ is phenyl substituted only at the para and meta positions with substituents independently selected from halogen and $C_1$-$C_3$ alkoxy.

In some embodiments of the compound of formula (II), Y is

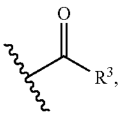

$R^3$ is cyclopropyl, $R^5$ is H, and $R^4$ is phenyl substituted only at the para and ortho positions with a halogen.

In some embodiments of the compound of formula (II), Y is

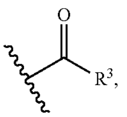

$R^3$ is cyclopropyl, $R^5$ is H, and $R^4$ is selected from the group consisting of $C_1$-$C_3$ alkyl substituted pyrazolyl; 2,3-dihydrobenzofuranyl; pyridinyl; thiophenyl; and benzodioxolyl.

In some embodiments of the compound of formula (II), Y is

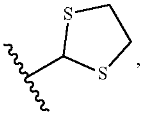 [SMILES: *C1SCCS1]

$R^4$ is phenyl, and $R^5$ is H.

In some embodiments of the compound of formula (II), Y is

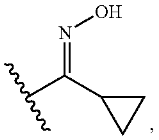 [SMILES: */C(=N/O)C1CC1]

$R^4$ is $C_1$-$C_3$ alkoxy, and $R_5$ is H.

In some embodiments of the compound of formula (II), Y is $NO_2$, $R_5$ is H, and $R^6$ is H or Me.

According to some embodiments, the compound of formula (II) is a compound having the following structure:

JSK3011

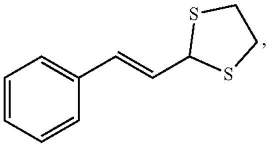

JSK3086

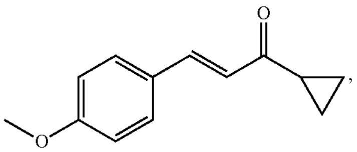

JSK3087

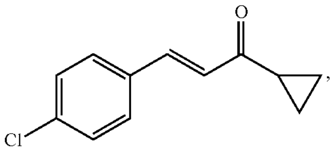

JSK3088

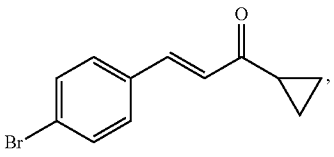

JSK3089

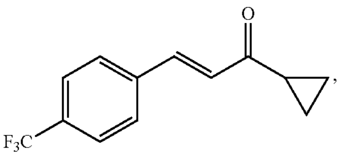

-continued

JSK3090

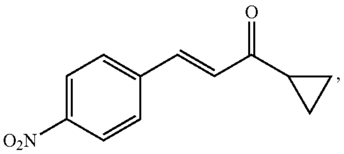

JSK3103

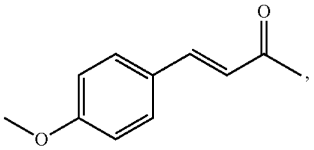

JSK3106

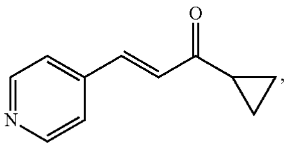

JSK3108

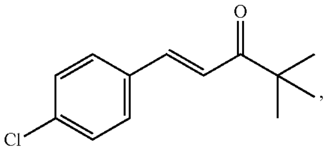

JSK3110

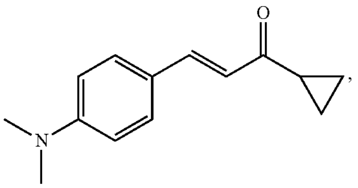

JSK3114

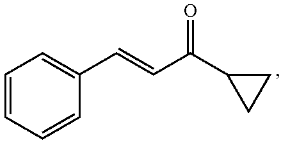

JSK3131

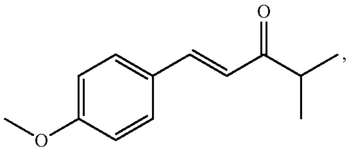

JSK3135

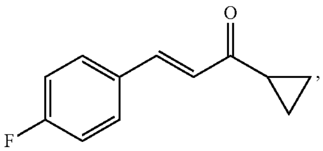

JSK3139

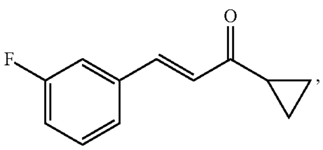

JSK3141

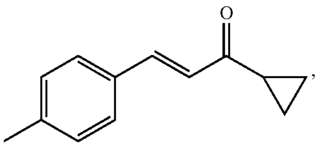

-continued
JSK3144
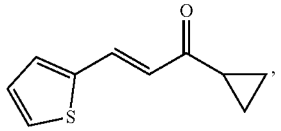,
JSK3145
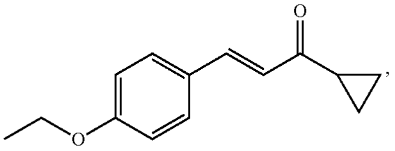,
JSK3206
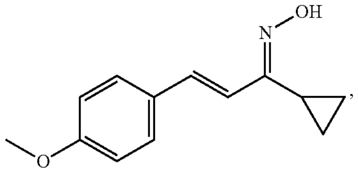,
JSK3271
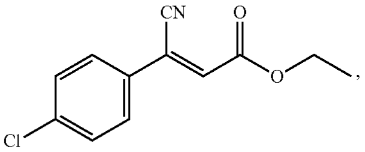,
JSK3272
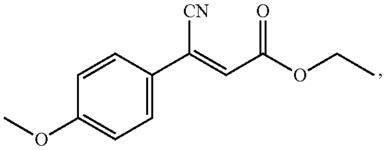,
JSK3285
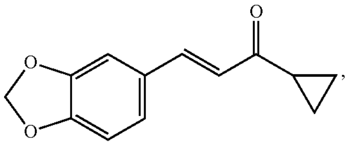,
JSK3295
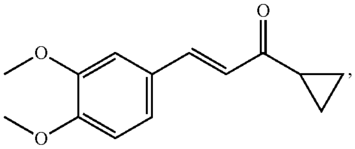,
JSK4012
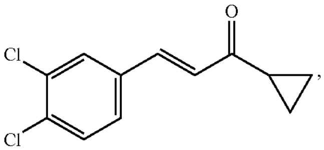,
JSK3091
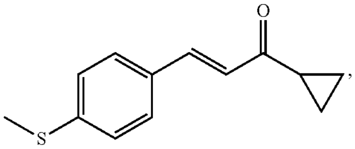,
JSK3142
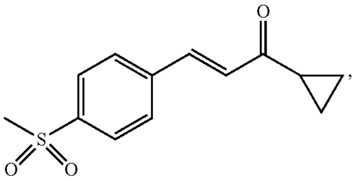,
-continued
JSK3169
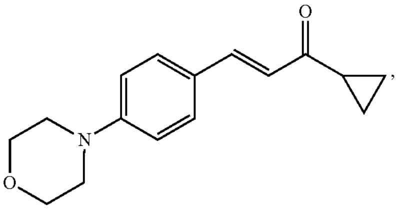,
JSK3209
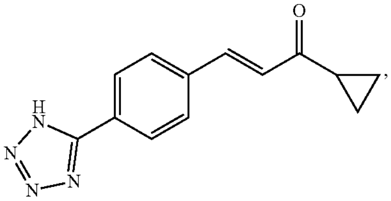,
JSK3294
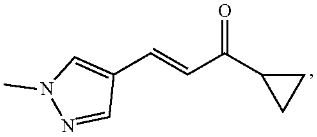,
JSK3296
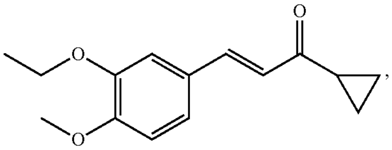,
JSK3297
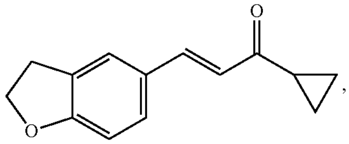,
JSK4018
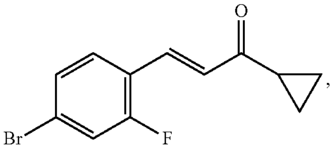,
JSK4044
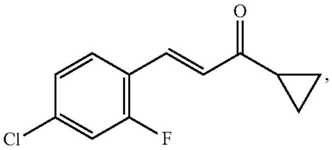,
JSK3275
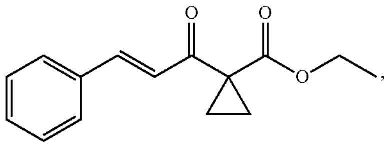,
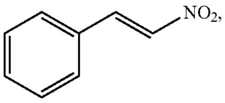,
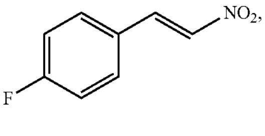, -continued

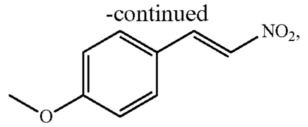

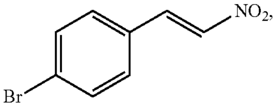 or

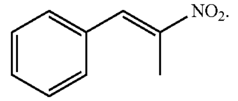

According to some embodiments, the compound of formula (II) is selected from

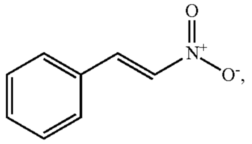

beta-nitrostyrene

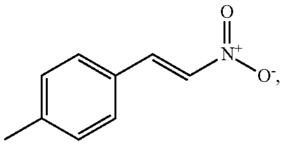 and 4-methyl beta-nitrostyrene

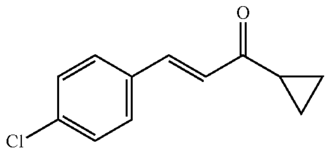

4-chloro styryl cyclopropyl ketone.

Compounds of formula (I) and formula (II) may be synthesized using methods known in the art.

For example, compounds of formula (I) may be synthesized utilizing an aldol condensation of an aldehyde and a ketone under basic conditions to form an α, β, unsaturated ketone (see Scheme 1).

Scheme 1. Exemplary synthetic route to compounds of formula (I).

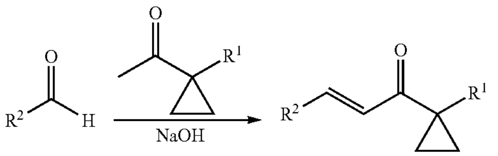

Compounds of formula (II), when Y is

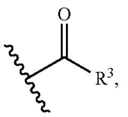

may also be formed form from aldol condensation of an aldehyde or ketone, with a ketone (e.g., 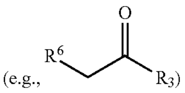)

in the presence of a suitable base, such as sodium hydroxide.

When compounds of formula (II) have a Y of

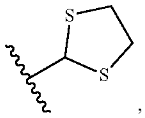 [SMILES: *C1SCCS1]

compounds of formula (II) may be formed from the condensation of an aldehyde (e.g., 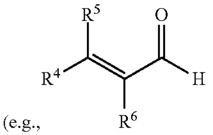)

with 1,2-ethanedithiol in the presence of a suitable Lewis acid catalyst, such as elemental iodine or boron trifluoride.

When Y is

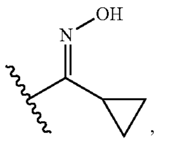 [SMILES: */C(=N/O)C1CC1]

compounds of formula (II) may be formed from the condensation of

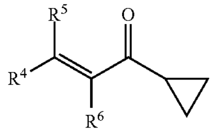

with hydroxylamine.

When Y is $NO_2$, compounds of formula (II) may be formed from the condensation of an aldehyde or ketone (e.g., 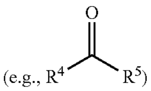)

with a nitro compound (e.g., 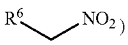)

in the presence of a suitable base, such as sodium hydroxide or triethylamine.

Exemplary synthetic routes to compounds of formula (II) are shown in Scheme 2.

Scheme 2. Exemplary synthetic routes to compounds of formula (II).

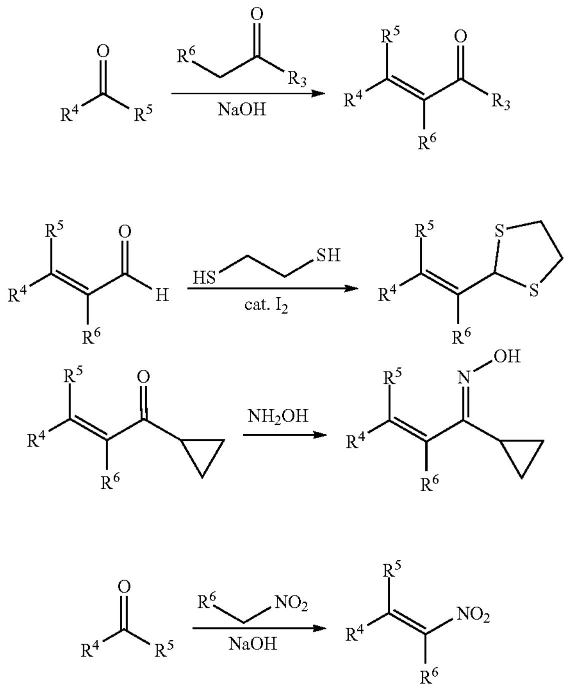

In some embodiments of carrying out said contacting, the compound of formula (II) is a nematicide. As used herein, the term "nematicide" means a compound that inhibits the growth of, inhibits the reproduction or reproductive cycle of, contains, prevents the growth or invasion of, or kills nematodes or nematode eggs or juveniles to contain, reduce, prevent, or eliminate nematode or nematode growth or reproduction in a growing media or on a plant or a plant part.

In some embodiments, said contacting is carried out simultaneously or nearly simultaneously with planting seed in a growing media. In other words, according to some embodiments, the method is carried out simultaneously with planting a seed vulnerable (at the seed or, more likely, the plant stage) to a nematode. According to this embodiment, treatment of a growing media may happen at or near the time the seed is planted in the growing media. Alternatively, treatment of the growing media with the compound of formula (II) may occur via a pre-treated seed (e.g., a coating on the seed that contains a compound of formula (II), which comes into contact with the growing media to be treated at the time of planting the seed in the growing media). Seed treatment with the compound of formula (II) can be combined with other seed treatments such as fungicides, insecticides, and bio-enhancers.

In some embodiments, said contacting involves contacting a plant or growing media with a compound of formula (II) that is a stimulant to a nematode. As used herein, the term "stimulant" means a compound that promotes the growth and/or development of nematodes or nematode eggs or juveniles.

In some embodiments, the compound of formula (II) may be any one or more of

JSK3133

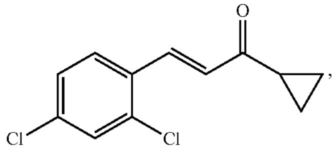,

JSK3092

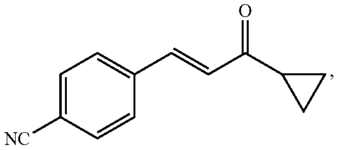, or

JSK3109

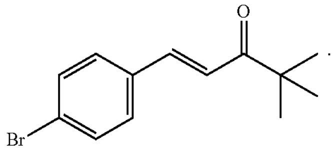.

In some embodiments, said contacting is carried out simultaneously or nearly simultaneously with planting a plant other than a plant vulnerable to a nematode. According to some embodiments, a compound of formula (II) may be effective in treating a nematode by promoting nematode growth and/or development in the absence of a critical plant host, which results in the inability of the nematode to grow, reproduce, hatch, or survive (death from starvation), thus reducing the presence of or eliminating the nematode from growing media to permit successful cultivation of plants vulnerable to a nematode in the treated growing media.

In carrying out the methods disclosed herein, contacting may be carried out by any suitable means, including those common in agricultural settings for application of chemicals to plants and/or growing media. Such methods include, without limitation, application to a plant, a growing media, soil, or planting area by high- or low-pressure spraying. Suitable application means may also include atomizing, foaming, fogging, coating, and encrusting. Contacting may be carried out using any formulation of the compounds described herein, including formulations of the compositions described infra.

A further aspect of the present application relates to a composition comprising:

a compound of formula (II) having the following structure:

(II)

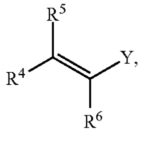, or a stereoisomer, salt, oxide, or solvate thereof, where

Y is

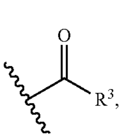, 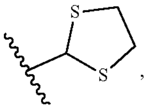, 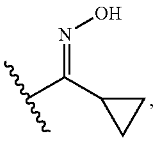, or $NO_2$;

$R^3$ is methyl, cyclopropyl, isopropyl, tert-butyl, $C_1$-$C_3$ alkoxy, or

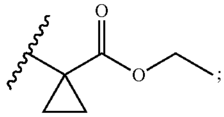 [SMILES: *C1(C(=O)OCC)CC1]

;

$R^4$ is selected from the group consisting of:

- phenyl;
- phenyl substituted only at the para position with a halogen, $CF_3$, $NO_2$, $S(C_1$-$C_3$ alkyl), CN, dimethylamine, $C_1$-$C_3$ alkyl, sulfonyl, $C_1$-$C_3$ alkoxy, morpholinyl, or tetrazolyl;
- phenyl substituted only at the meta position with a halogen;
- phenyl substituted only at the para and meta positions with substituents independently selected from halogen and $C_1$-$C_3$ alkoxy;
- phenyl substituted only at the para and ortho positions with a halogen;
- $C_1$-$C_3$ alkyl substituted pyrazolyl;
- 2,3-dihydrobenzofuranyl;
- pyridinyl;
- thiophenyl; and
- benzodioxolyl; and $R^5$ is H or CN;

$R^6$ is H or Me and an agriculturally acceptable carrier.

According to some embodiments, the composition is formulated into any suitable form including, without limitation, a solution, emulsion, emulsifiable concentrate, suspension, foam, paste, aerosol, suspoemulsion concentrate, slurry, dry powder, granule, or pellet. Suitable compositions may include, for example and without limitation, those for HV, LV, and ULV spraying and for ULV cool and warm fogging formulations. In some embodiments, the composition is formulated in a manner suitable for large or small scale agricultural and horticultural applications.

Compositions may be prepared and produced in a known manner, for example, by mixing a liquid composition with extenders, that is, liquid solvents, liquefied gases under pressure, and/or solid carriers. Wetting agents and/or surfactants, that is, emulsifiers and/or dispersants, sequestering agents, plasticizers, brighteners, flow agents, coalescing agents, waxes, fillers, polymers, anti-freezing agents, biocides, thickeners, tackifiers, and/or foam formers and defoaming agents may also be used in manners commonly known by those of ordinary skill in the art. If the extender used is water, it is also possible to employ, for example, organic solvents as auxiliary solvents. Other possible additives are mineral and vegetable oils, colorants such as inorganic pigments, and trace nutrients.

The nature and action of such additives are well-known to those of ordinary skill in the art of liquid formulations. Additives should not interfere with the action of a compound of formula (II) or any other biologically active component that may be included in the formulation.

The active compound(s) content of the composition (e.g., one or more compounds of formula (II)) may vary within a wide range. For example, the concentration of active compound (i.e., one or more compounds of formula (II)) may be from 0.0000001 to 20% by weight, or from 0.0001 to 15% by weight.

In some embodiments, it may be desirable to combine the composition of the present application with effective amounts of other agricultural or horticultural chemicals, such as herbicides (e.g., glyphosate), insecticides, acaricides, other nematicides, molluscicides, attractants, sterilants, bactericides, fungicides, and/or growth regulators.

One common herbicide is glyphosate, commonly known as 2 (phosphonomethylamino)acetic acid. Glyphosate salts may also be used. Suitable glyphosate salts include, for example, but are not limited to, isopropylamine salts, diammonium salts, and trimethylsulfonium salts. Mixtures including glyphosate typically include one or more surfactants, typically one or more nonionic surfactants, though no surfactant should be required. Glyphosate-containing formulations are typically applied to desirable plants and plant-parts that are glyphosate resistant.

Examples of other herbicides that may be useful in compositions described herein include, for example, but are not limited to: amide herbicides, including allidochlor, amicarbazone, beflubutamid, benzadox, benzipram, bromobutide, cafenstrole, CDEA, cyprazole, dimethenamid, dimethenamid-P, diphenamid, epronaz, etnipromid, fentrazamide, flucarbazone, flupoxam, fomesafen, halosafen, isocarbamid, isoxaben, napropamide, naptalam, pethoxamid, propyzamide, quinonamid, saflufenacil, and tebutam; anilide herbicides, including chloranocryl, cisanilide, clomeprop, cypromid, diflufenican, etobenzanid, fenasulam, flufenacet, flufenican, ipfencarbazone, mefenacet mefluidide, metamifop, monalide, naproanilide, pentanochlor, picolinafen, propanil, sulfentrazone; arylalanine herbicides, including benzoylprop, flamprop, and flamprop-M; chloroacetanilide herbicides, including acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor, and xylachlor; sulfonanilide herbicides, including benzofluor, cloransulam, diclosulam, florasulam, flumetsulam, metosulam, perfluidone, pyrimisulfan, and profluazol; sulfonamide herbicides, including asulam, carbasulam, fenasulam, oryzalin, penoxsulam, and pyroxsulam; thioamide herbicides, including bencarbazone and chlorthiamid; antibiotic herbicides, including bilanafos; aromatic acid herbicides; benzoic acid herbicides, including chloramben, dicamba, 2,3,6-TBA, and tricamba; pyrimidinyloxybenzoic acid herbicides, including bispyribac and pyriminobac; pyrimidinylthiobenzoic acid herbicides, including pyrithiobac; phthalic acid herbicides, including chlorthal, picolinic acid herbicides, aminopyralid, clopyralid, and picloram; quinolinecarboxylic acid herbicides, including quinclorac and quinmerac; arsenical herbicides, including cacodylic acid, CMA, DSMA, hexaflurate, MAA, MAMA, MSMA, potassium arsenite, and sodium arsenite; benzoylcyclohexanedione herbicides, including mesotrione, sulcotrione, tefuryltrione, and tembotrione; benzofuranyl alkyl sulfonate herbicides, including benfuresate and ethofumesate; benzothiazole herbicides, including benazolin, benzthiazuron, fenthiaprop, mefenacet, and methabenzthiazuron; carbamate herbicides, including asulam, carboxazole, chlorprocarb, dichlormate, fenasulam, karbutilate, and terbucarb; carbanilate herbicides, including barban, BCPC, carbasulam, carbetamide, CEPC, chlorbufam, chlorpropham, CPPC, desmedipham, phenisopham, phenmedipham, phenmedipham-ethyl, propham, and swep; cyclohexene oxime herbicides, including alloxydim, butroxydim, clethodim, cloproxydim, cycloxydim, profoxydim, sethoxydim, tepraloxydim, and tralkoxydim; cyclopropylisoxazole herbicides, including isoxachlortole and isoxaflutole; dicarboximide herbicides, including cinidon-ethyl, flumezin, flumiclorac, flumioxazin, and flumipropyn; dinitroaniline herbicides, including benfluralin, butralin, dinitramine, ethalfluralin, fluchloralin, isopropalin, methalpropalin, nitralin, oryzalin, pendimethalin, prodiamine, profluralin, and trifluralin; dinitrophenol herbicides, including dinofenate, dinoprop, dinosam, dinoseb, dinoterb, DNOC, etinofen, and medinoterb; diphenyl ether herbicides, including ethoxyfen; nitrophenyl ether herbicides, including acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen, and oxyfluorfen; dithiocarbamate herbicides, including dazomet and metam; halogenated aliphatic herbicides, including alorac, chloropon, dalapon, flupropanate, hexachloroacetone, iodomethane, methyl bromide, monochloroacetic acid, SMA, and TCA; imidazolinone herbicides, including imazamethabenz, imazamox, imazapic, imazapyr, imazaquin, and imazethapyr; inorganic herbicides, including ammonium sulfamate, borax, calcium chlorate, copper sulfate ferrous sulfate, potassium azide, potassium cyanate, sodium azide, sodium chlorate, and sulfuric acid; nitrile herbicides, including bromobonil, bromoxynil, chloroxynil, dichlobenil, iodobonil, ioxynil, and pyraclonil; organophosphorus herbicides, including amiprofos-methyl, anilofos, bensulide, bilanafos, butamifos, 2,4-DEP, DMPA, EBEP, fosamine, glufosinate, glufosinate-P, glyphosate, and piperophos; oxadiazolone herbicides, including dimefuron, methazole, oxadiargyl, and oxadiazon; oxazole herbicides, including carboxazole, isouron, isoxaben, isoxachlortole, isoxaflutole, monisouron, pyroxasulfone, and topramezone; phenoxy herbicides, including bromofenoxim, clomeprop, 2,4-DEB, 2,4-DEP, difenopenten, disul, erbon, etnipromid, fenteracol, and trifopsime; phenoxyacetic herbicides, including 4-CPA, 2,4-D, 3,4-DA, MCPA, MCPA-thioethyl, and 2,4,5-T; phenoxybutyric herbicides, including 4-CPB, 2,4-DB, 3,4-DB, MCPB, and 2,4,5-TB; phenoxypropionic herbicides, including cloprop, 4-CPP, dichlorprop, dichlorprop-P, 3,4-DP, fenoprop, mecoprop, and mecoprop-P; aryloxyphenoxypropionic herbicides, including chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, and trifop; phenylenediamine herbicides, including dinitramine, and prodiamine; pyrazole herbicides, including azimsulfuron, difenzoquat, halosulfuron, metazachlor, pyrazosulfuron, and pyroxasulfone; benzoylpyrazole herbicides, including benzofenap, pyrasulfotole, pyrazolynate, pyrazoxyfen, and topramezone; phenylpyrazole herbicides, including fluazolate, nipyraclofen, and pyraflufen; pyridazine herbicides, including credazine, pyridafol, and pyridate; pyridazinone herbicides, including brompyrazon, chloridazon, dimidazon, flufenpyr, metflurazon, norflurazon, oxapyrazon, and pydanon; pyridine herbicides, including aminopyralid, cliodinate, clopyralid, diflufenican, dithiopyr, flufenican, fluroxypyr, haloxydine, picloram, picolinafen, pyriclor, pyroxsulam, thiazopyr, and triclopyr; pyrimidinediamine herbicides, including iprymidam and tioclorim; quaternary ammonium herbicides, including cyperquat, diethamquat, difenzoquat, diquat, morfamquat, and paraquat; thiocarbamate herbicides, including butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate, and vernolate; thiocarbonate herbicides, including dimexano, EXD, and proxan; thiourea herbicides, including methiuron; triazine herbicides, including dipropetryn, triaziflam, and trihydroxytriazine; chlorotriazine herbicides, including atrazine, chlorazine, cyanazine, cyprazine, eglinazine, ipazine, mesoprazine, procyazine, proglinazine, propazine, sebuthylazine, simazine, terbuthylazine, and trietazine; methoxytriazine herbicides, including atraton, methometon, prometon, secbumeton, simeton, and terbumeton; methylthiotriazine herbicides, including ametryn, aziprotryne, cyanatryn, desmetryn, dimethametryn, methoprotryne, prometryn, simetryn, and terbutryn; triazinone herbicides, including ametridione, amibuzin, hexazinone, isomethiozin, metamitron, and metribuzin; triazole herbicides, including amitrole, cafenstrole, epronaz, and flupoxam; triazolone herbicides, including amicarbazone, bencarbazone, carfentrazone, flucarbazone, ipfencarbazone, propoxycarbazone, sulfentrazone, and thiencarbazone; triazolopyrimidine herbicides, including cloransulam, diclosulam, florasulam, flumetsulam, metosulam, penoxsulam, and pyroxsulam; uracil herbicides, including benzfendizone, bromacil, butafenacil, flupropacil, isocil, lenacil, saflufenacil, and terbacil; urea herbicides, including benzthiazuron, cumyluron, cycluron, dichloralurea, diflufenzopyr, isonoruron, isouron, methabenzthiazuron, monisouron, and noruron; phenylurea herbicides, including anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron, and thidiazuron; sulfonylurea herbicides; pyrimidinylsulfonylurea herbicides, including amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron, and trifloxysulfuron; triazinylsulfonylurea herbicides, including chlorsulfuron, cinosulfuron, ethametsulfuron, iodosulfuron, metsulfuron, prosulfuron, thifensulfuron, triasulfuron, tribenuron, triflusulfuron, and tritosulfuron; thiadiazolylurea herbicides, including buthiuron, ethidimuron, tebuthiuron, thiazafluron, and thidiazuron; and unclassified herbicides, including acrolein, allyl alcohol, aminocyclopyrachlor, azafenidin, bentazone, benzobicyclon, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, flurochloridone, flurtamone, fluthiacet, indanofan, methyl isothiocyanate, OCH, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan, and tritac. The above list is exemplary only and other herbicides may also be used in conjunction with the compositions disclosed herein.

Examples of specific insecticides, acaricides, nematicides, and molluscicides that may be used in compositions taught herein include, but are not limited to: abamectin, acephate, acetamiprid, acrinathrin, alanycarb, aldicarb, alpha-cypermethrin, alphamethrin, amitraz, azinphos A, azinphos-methyl, azocyclotin, bendiocarb, benfuracarb, bensultap, beta cyfluthrin, bifenthrin, brofenprox, bromophos A, bufencarb, buprofezin, butocarboxin, butylpyridaben, cadusafos, carbaryl, carbofuran, carbophenothion, carbosulfan, cartap, chloethocarb, chloranthraniliprole, chlorethoxyfos, chlorfenvenphos, chlorfluazuron, chlormephos, chlorpyrifos, cis-resmethrin, clocythrin, clofentezin, clothianidin, cyanimine, cyanophos, cycloprothrin, cyfluthrin, cyhexatin, deltamethrin, demeton M, demeton S, demeton-S-methyl, diafenthiuron, dibutylaminothion, dichlofenthion, dicliphos, diethion, diflubenzuron, dimethoate, dimethylvinphos, dinotefuran, dioxathion, doramectin, edifenphos, emamectin, endosulfan, esfenvalerate, ethiofencarb, ethion, ethiprole, etofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flubendiamide, flucycloxuron, flucythrinate, flufenoxuron, flufenprox, fluxofenime, fonophos, formothion, fosthiazate, fubfenprox, gamma cyhalothrin, HCH, heptenophos, hexaflumuron, hexythiazox, imidacloprid, iprobenfos, isoprocarb, isoxathion, ivermectin, lambda cyhalothrin, lindane, lufenuron, malathion, mecarbam, mesulfenphos, metaldehyde, methamidophos, methiocarb, methomyl, metolcarb, mevinphos, milbemectin, milbemycin oxime, moxidectin, naled, NC 184, nitenpyram, nitromethylene, omethoate, oxamyl, oxydemethon M, oxydeprofos, parathion, parathion-methyl, permethrin, phenthoate, phorate, phosalone, phosmet, phoxim, pirimicarb, pirimiphos A, pirimiphos M, promecarb, propaphos, propoxur, prothiofos, prothoate, pymetrozine, pyrachlophos, pyradaphenthion, pyresmethrin, pyrethrum, pyridaben, pyrimidifen, pyripfoxyfen, pyriproxyfen, rynaxypyr, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiacloprid, thiafenox, thiamethoxam, thiodicarb, thiofanox, thionazin, thuringiensin, tralomethrin, triarthen, triazamate, triazophos, triazuron, trichlorofon, triflumuron, trimethacarb, vamidothion, xylylcarb, zeta-cypermethrin, zetamethrin, and *Bacillus thuringiensis* (Bt) products, including the salts and esters thereof. The above list is exemplary only and other insecticides may also be used in conjunction with the compositions disclosed herein.

A variety of fungicides may be used in embodiments of the compositions disclosed herein. They include, for example and without limitation, those classified and listed by the Fungicide Resistance Action Committee (FRAC), *FRAC CODE LIST* 1: *Fungicides sorted by FRAC Code*, December 2006, which is hereby incorporated by reference in its entirety. A summary of this list includes: methyl benzimidazole carbamates (MBC): e.g., benzimidazoles and thiophanates; dicarboximides; demethylation inhibitors (DMI) (SBI: Class I): e.g., imidazoles, piperazines, pyridines, pyrimidines, and triazoles; phenylamides (PA): e.g., acylalanines, oxazolidinones, and butyrolactones; amines (SBI: Class II): e.g., morpholines, piperidines, and spiroketalamines; phosphoro-thiolates and dithiolanes; carboxamides: e.g., benzamides, furan carboxamides, oxathiin carboxamides, thiazole carboxamides, pyrazole carboxamides, and pyridine carboxamides; hydroxy-(2-amino-) pyrimidines; anilino-pyrimidines (AP); N-phenyl carbamates; quinone outside inhibitors (Qol): e.g., methoxyacrylates, methoxy-carbamates, oximino acetates, oximino-acetamides, oxazolidine-diones, dihydro-dioxazines, imidazolinones, and benzyl-carbamates; phenylpyrroles; quinolines; aromatic hydrocarbons (AH) and heteroaromatics I: e.g., 1,2,4-thiadiazoles; cinnamic acids; melanin biosynthesis inhibitors-reductase (MBI-R): e.g., isobenzofuranone, pyrroloquinolinone, and triazolobenzo-thiazole; melanin biosynthesis inhibitors-dehydratase (MBI-D): e.g., cyclopropane-carboxamide, carboxamide, and propionamide; hydroxyanilides (SBI: Class III); hydroxyanilides (SBI: Class IV): e.g., thiocarbamates and allylamines; polyoxins: e.g., peptidyl pyrimidine nucleoside; phenylureas; quinone inside inhibitors (QiI): e.g., cyanoimidazole and sulfamoyl-triazoles; benzamides: e.g., toluamides; antibiotics: e.g., enopyranuronic acid, hexopyranosyl, streptomycin, and validamycin; cyanoacetamide-oximes; carbamates; dinitrophenyl crotonates; pyrimidinone-hydrazones; 2,6-dinitro-anilines; organo tin compounds: e.g., triphenyl tin compounds; carboxylic acids; heteroaromatics II: e.g., isoxazoles and isothiazolones; phosphonates: e.g., ethyl phosphonates and phosphorous acid and salts; phthalamic acids; benzotriazines; benzene-sulfonamides; pyridazinones; thiophene-carboxamides; pyrimidinamides; CAA-fungicides (carboxylic acid amides): e.g., cinnamic acid amides, valinamide carbamates and mandelic acid amides; tetracycline; thiocarbamate; benzamides: e.g., acylpicolides; host plant defense inducers: e.g., benzo-thiadiazole BTH, benzisothiazole and thiadiazole-carboxamides; unclassified materials: e.g., thiazole carboxamide, phenyl-acetamide, quinazolinone, and benzophenone; multi-site contact materials: e.g., copper salts, sulfur, dithiocarbamates and relatives, phthalimides, chloronitriles (phthalonitriles), sulphamides, guanidines, triazines, and quinones (anthraquinones); non-classified materials: e.g., mineral oils, organic oils, potassium bicarbonate, and biological materials. Those skilled in the art will recognize that use of other fungicides is also possible in various embodiments of the present application.

The compositions disclosed herein may contain additional additives, such as a fertilizer.

In some embodiments, compositions described herein may be microencapsulated in a polymeric substance. Examples of suitable microencapsulation materials include the following classes of materials for which representative members are provided. It will be apparent to those skilled in the art that other classes of materials with polymeric properties may be used and that other materials within each given class and others polymeric classes may be used for microencapsulation. In this description, microencapsulation is taken to include methods and materials for nanoencapsulation. Examples include but are not limited to: gums and natural macromolecules, such as gum arabic, agar, sodium alginate, carageenan, and gelatin; carbohydrates, such as starch, dextran, sucrose, corn syrup, and β-cyclodextrin; celluloses and semisynthetic macromolecules, such as carboxymethylcellulose, methycellulose, ethylcellulose, nitrocellulose, acetylcellulose, cellulose acetate-phthalate, cellulose acetate-butylate-phthalate, epoxy, and polyester; lipids such as wax, paraffin, stearic acid, monoglycerides, phospholipids, diglycerides, beeswax, oils, fats, hardened oils, and lechitin; inorganic materials, such as calcium sulfate, silicates, and clays; proteins, such as gluten, casein, gelatin, and albumin; biological materials, such as voided cells from organisms like baker's yeast and other microorganisms together with other formerly living cell tissues. Furthermore, these materials may be used singly or compounded in the processes of micro- or nano-encapsulation.

In some embodiments, one or more compounds of formula (II) can be applied to plant seeds (e.g., as a seed coating) with other conventional seed formulation and treatment materials including, without limitation, clays and polysaccharides.

Compositions disclosed herein may be applied, e.g., to a plant, a growing media, soil, or planting area, by high- or low-pressure spraying. Suitable application means may also include atomizing, foaming, fogging, coating, and encrusting.

When treating plant seeds, the composition can be applied by low- or high-pressure spraying, coating, or immersion. Other suitable application procedures can be envisioned by those skilled in the art. Once soil, growing medium, or a plant seed is treated with the composition, seeds can be planted and cultivated using conventional procedures to produce plants. After plants have been propagated from seeds, soil, or growing medium treated with compositions disclosed herein, the soil or growing medium may be treated with one or more applications of the composition described herein to impart disease resistance to plants, to enhance plant growth, to control disease on the plants, and/or impart stress resistance.

In some embodiments, application of the composition is to soil or a growing medium for plants vulnerable to nematode disease. Applying the composition to a soil or a growing medium may be carried out at a rate of about 0.1 to 10,000 g/ha of a composition disclosed herein.

In another embodiment, application of the composition is to plant seed. Applying the composition to a plant seed may be carried out at a rate of about 0.001 to 50 g/kg of the composition to seed.

Another aspect of the present application relates to a method of treating a plant or a growing media for a nematode. This method involves contacting a plant or a growing media with a compound having a structure

JSK1132

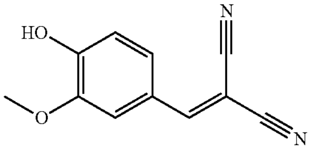

to treat the plant or growing media for the nematode.

In some embodiments, said contacting is carried out simultaneously with planting seed in the growing media.

In some embodiments, said contacting is carried out simultaneously with planting seed in the growing media.

These aspects of the present application are further illustrated by the examples below.

EXAMPLES

Example 1—Syntheses of Representative Compounds

Synthesis of JSK 3087 (4-Chlorostyryl Cyclopropyl Ketone)

JSK3087

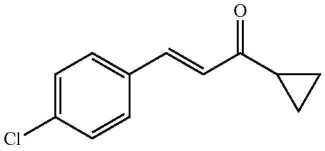

4-Chlorobenzaldehyde (14.06 g, 100 mmol) and cyclopropyl methyl ketone (10.09 g, 120 mmol) were dissolved in ethanol (100 mL) and water (25 mL), and 1 M sodium hydroxide (10 mL) was added while the reaction was stirred at room temperature. After the completion of the reaction as monitored by thin-layer chromatography, the crude product was extracted from the reaction mixture with ethyl acetate, and the organic extract was washed with water and brine. The solvent was removed under vacuum, and the crude 4-chlorostyryl cyclopropyl ketone was recrystallized from heptane to yield 16.3 g of white crystals.

Synthesis of JSK 3086 (4-Methoxystyryl Cyclopropyl Ketone)

JSK3086

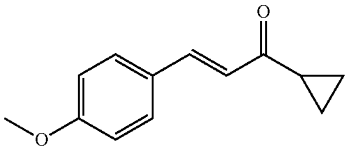

4-Anisaldehyde (2.72 g, 20 mmol) and cyclopropyl methyl ketone (2.02 g, 24 mmol) were dissolved in ethanol (20 mL) and water (5 mL). 1 M sodium hydroxide (1 mL) was added, and the reaction was stirred at room temperature overnight, during which time a white solid formed. The reaction was diluted with water (100 mL) and cooled to 0° C., and the solid was filtered off. The crude solid was dried and recrystallized from 9:1 hexane:ethyl acetate to yield pale yellow crystals (3.64 g).

Synthesis of JSK 3091 (4-(Methylthio)Styryl Cyclopropyl Ketone)

JSK3091

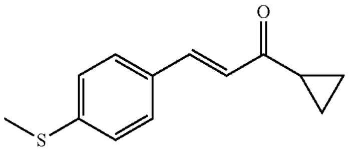

4-(Methylthio)benzaldehyde (3.04 g, 20 mmol) and cyclopropyl methyl ketone (2.02 g, 24 mmol) were dissolved in ethanol (20 mL) and water (5 mL). 1 M sodium hydroxide (1 mL) was added, and the reaction was stirred at room temperature overnight. The reaction was diluted with water (100 mL) and cooled to 0° C., and extracted twice with 1:1 hexane:ethyl acetate. The combined organic layers were washed with water, then 1 M sodium hydroxide, then brine, and dried over anhydrous magnesium sulfate. After removing the solvent, the 4-(methylthio)styryl cyclopropyl ketone was purified by column chromatography (9:1 hexane:ethyl acetate) to yield yellow crystals (1.98 g).

Synthesis of JSK 3139 (3-Fluorostyryl Cyclopropyl Ketone)

JSK3139

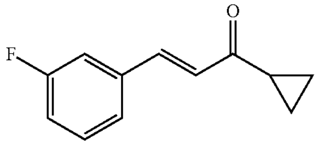

3-Fluorobenzaldehyde (2.48 g, 20 mmol) and cyclopropyl methyl ketone (2.02 g, 24 mmol) were dissolved in ethanol (20 mL) and water (5 mL). 1 M sodium hydroxide (1 mL) was added, and the reaction was stirred at room temperature overnight, during which time the reaction became biphasic. The reaction was diluted with water (100 mL) and extracted twice with ethyl acetate. The combined organic layers were washed with water, then 1 M sodium hydroxide, then brine, and dried over anhydrous magnesium sulfate. After removing the solvent, the 3-fluorostyryl cyclopropyl ketone was purified by column chromatography (9:1 hexane:ethyl acetate).

Synthesis of JSK 3296 (3-Ethoxy-4-Methoxystyryl Cyclopropyl Ketone)

JSK3296

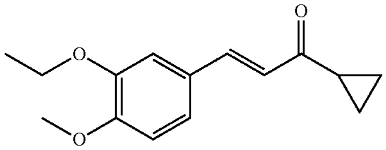

Ethylvanillin (1.09 g, 8 mmol) and cyclopropyl methyl ketone (1.68 g, 16 mmol) were dissolved in ethanol (10 mL) and water (3 mL). 1 M sodium hydroxide (1 mL) was added, and the reaction was stirred at room temperature overnight, during which time the reaction became biphasic. The reaction was diluted with water (50 mL) and extracted twice with ethyl acetate. The combined organic layers were washed with water, then 1 M sodium hydroxide, then brine, and dried over anhydrous magnesium sulfate. After removing the solvent, the 3-ethoxy-4-methoxystyryl cyclopropyl ketone was recrystallized from heptane/toluene to yield 1.31 g pale yellow crystals.

Synthesis of JSK 3169 (4-Morpholinostyryl Cyclopropyl Ketone)

JSK3169

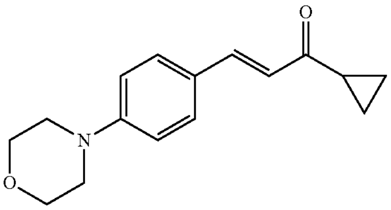

4-Morpholinobenzaldehyde (1.91 g, 10 mmol) and cyclopropyl methyl ketone (2.52 g, 30 mmol) were dissolved in isopropanol (50 mL), and 10 M sodium hydroxide (10 mL) was added. The biphasic reaction was stirred at 50° C. overnight, during which time the reaction became biphasic. The reaction was diluted with water (100 mL) and extracted twice with ethyl acetate. The combined organic layers were washed with water, then 1 M sodium hydroxide, then brine, and dried over anhydrous magnesium sulfate. After removing the solvent, the 4-morpholinostyryl cyclopropyl ketone was recrystallized from heptane to yield 1.64 g bright yellow crystals.

Synthesis of JSK 4018 (4-Bromo-2-Fluorostyryl Cyclopropyl Ketone)

JSK4018

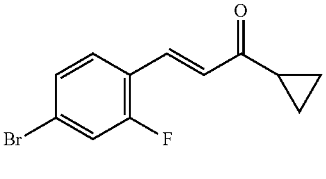

4-Bromo-2-fluorobenzaldehyde (2.03 g, 10 mmol) and cyclopropyl methyl ketone (1.01 g, 12 mmol) were dissolved in ethanol (20 mL) and water (5 mL). 1 M sodium hydroxide (1 mL) was added, and the reaction was stirred at room temperature overnight. The reaction was diluted with water (100 mL) and cooled to 0° C., and the solid was filtered off. The crude solid was dried and recrystallized from 9:1 hexane to yield light beige crystals (2.37 g).

Synthesis of JSK 3275 (Ethyl 1-Cinnamoylcyclopropane-1-Carboxylate)

JSK3275

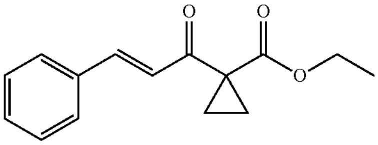

Benzaldehyde (1.06 g, 10 mmol) and ethyl 1-acetylcyclopropane-1-carboxylate (1.87 g, 12 mmol) were dissolved in 50 mL ethanol, and 1 M sodium hydroxide (5 mL) was added. The reaction was stirred overnight at room temperature, diluted with water (100 mL), and then extracted with ethyl acetate. The organic phase was washed with water, and then brine, and dried over magnesium sulfate. The solvent was removed, and the crude material was purified by column chromatography (9:1 hexane:ethyl acetate) to give white, lustrous crystals (1.68 g).

Example 2—Bioassay Data for Experimental Nematicides

Materials and Methods

Compounds

Several tested compounds were obtained commercially while others were synthesized from simple starting materials (see Example 1, supra). Compounds were dissolved in a solvent containing 0.08% ethanol, 0.08% TRITON™ X-100, and nano-purified water and were tested at 10 and 100 ppm.

SCN Hatching Assay

Figure 1B:

Two similar assays ran synchronously. For both, approximately 300 eggs were pipetted onto 20 mm-diameter plastic microsieves and placed in a six-well plate and incubated at 25° C. in 3 mL of treatment (FIG. 1A). In a continuous exposure assay, eggs (FIG. 1B) were incubated in treatments for 15 days, and in a short-term exposure assay, eggs were incubated in treatments for one day, rinsed, then incubated in deionized water for 14 days. The number of hatched second-stage juveniles (FIG. 1B) was determined for both assays after 3, 6, 9, 12, and 15 days when the microsieves containing the eggs were moved to an empty well and fresh treatment solution was added. Deionized water, 5.5 mM zinc sulfate, and the solvent were used as controls, and hatching was calculated relative to the solvent. Compounds were tested over twelve different experimental runs in total, with some tested three times, others twice, and some once.

Data Analysis I

The number of hatched and unhatched juveniles of SCN in each treatment were subjected to an analysis with a quasibinomial generalized linear model to estimate the percent hatching for each treatment in each individual experimental run. Then, a test of marginal means was done to determine the estimated percent hatching in each treatment over all runs. Finally, each estimated treatment percent was compared to the estimate of the solvent control and treatments with an estimated hatch proportion that were significantly greater and less than the solvent control reference level were identified. Analysis were performed on four different treatment groups: continuous 100 ppm, short term 100 ppm, continuous 10 ppm, and short term 10 ppm.

RKN Quick Sand Assay

Figure 2A:
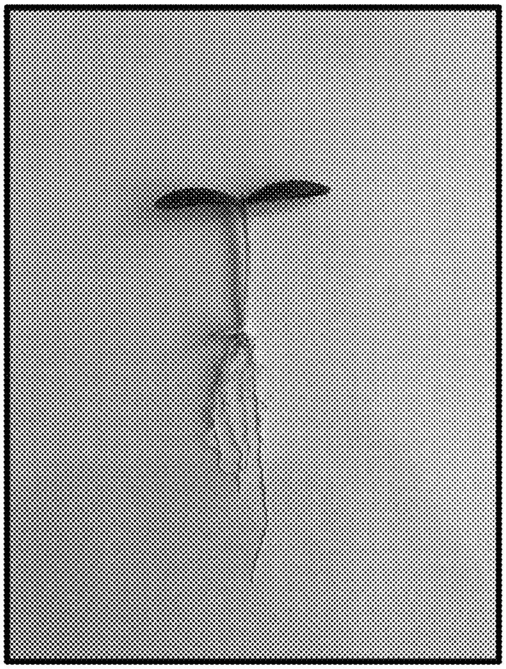
FIGS. 2A-C are photographs showing three main steps of the quick sand assay.
Figure 2B:
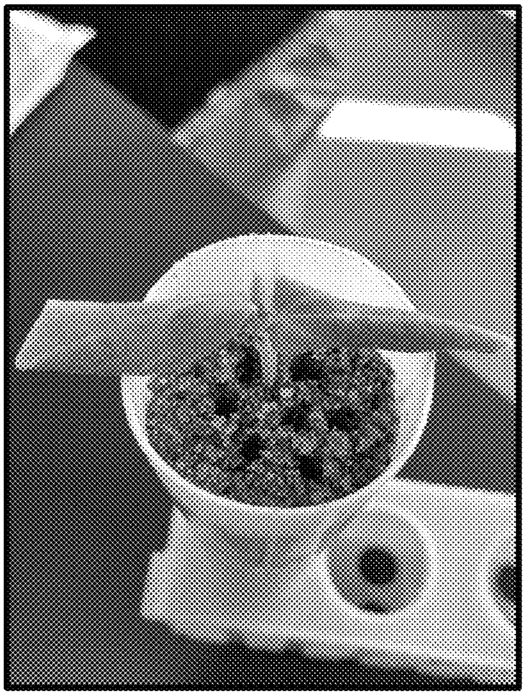
Figure 2C:
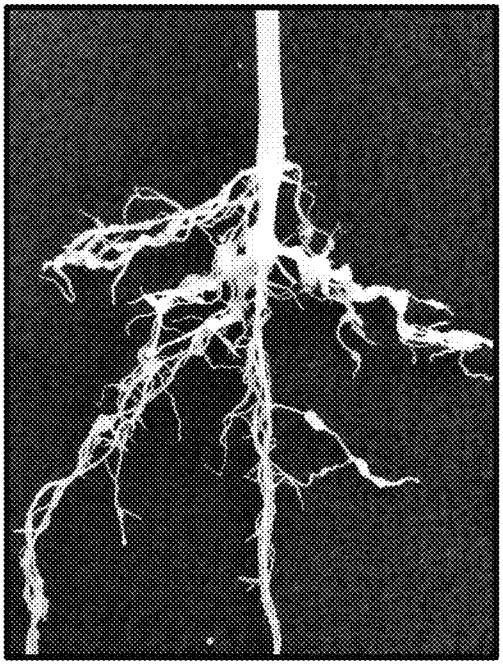
Figure 3A:
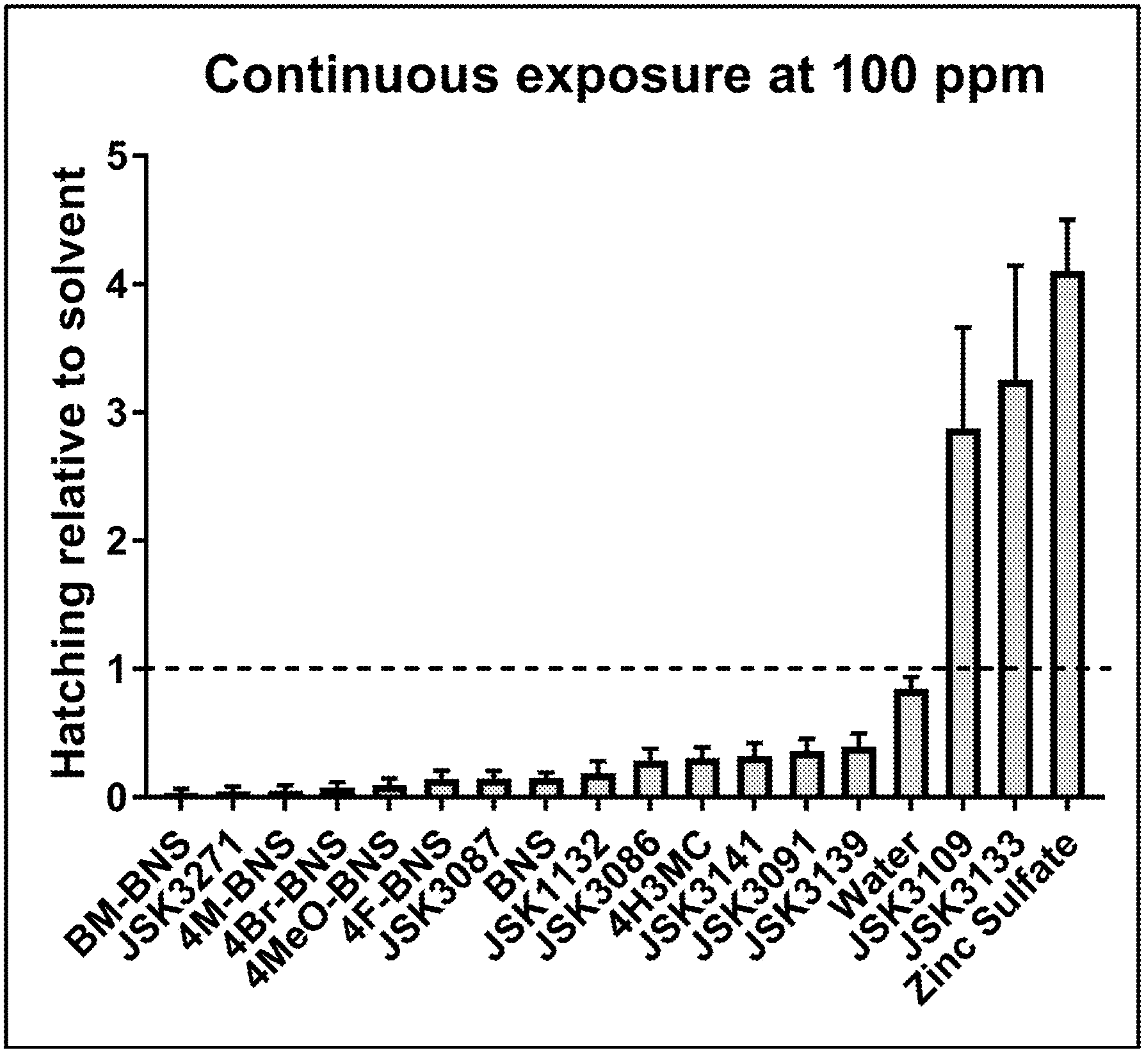
FIGS. 3A-D are graphs showing the effects of synthetic analogs of monoterpenes on SCN hatching after 15 days.
Figure 3B:
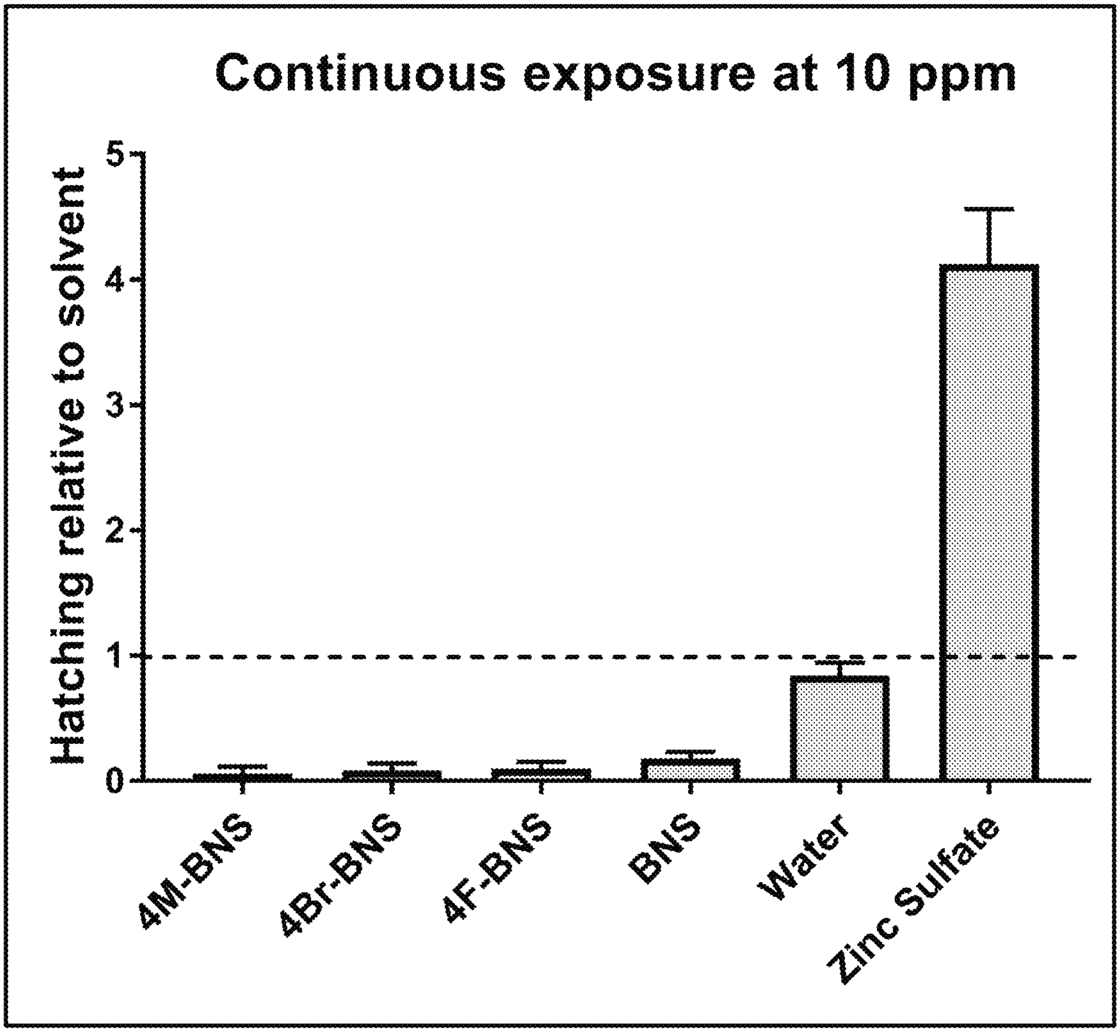
Figure 3C:
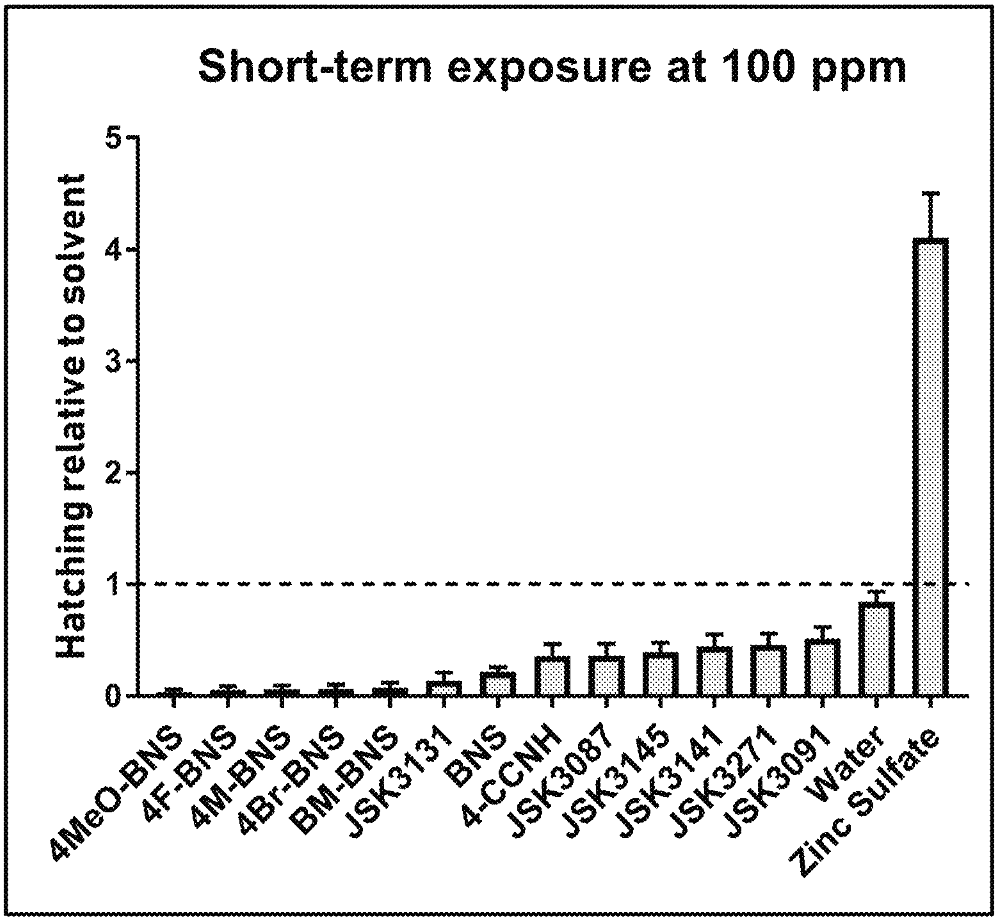
Figure 3D:
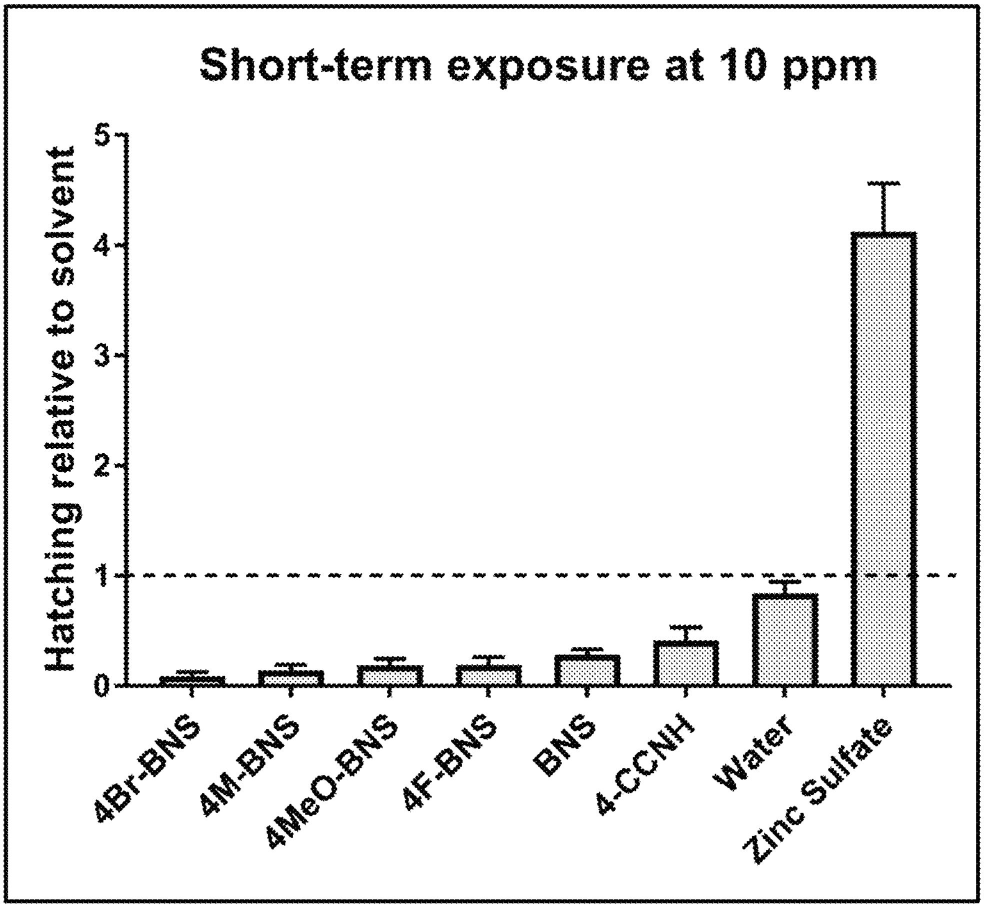

Cucumber seeds were planted in cone-tainers containing sterilized sand and grown for 12 days (FIG. 2A), after which 20 ml of the treatments were applied as a drench followed by infestation with 2,000 eggs of M. incognita suspended in water (FIG. 2B). Deionized water, 100 ppm abamectin, and solvent were used as controls. At 15 days after infestation, cucumber roots were washed, and the percentage of root galling caused by M incognita was assessed and compared to galling in the solvent control (FIG. 2C). To date, compounds were tested in three different experimental runs, with some compounds being tested twice and others once.

Data Analysis II

A beta regression model was used to estimate the percent of galling for each treatment in each run. As with the hatching data analyses, a test of marginal means was performed to determine the estimated percent of galling in each treatment over all runs. Finally, each estimated treatment percentage was compared to the estimate of the solvent control, and treatments with an estimated galling proportion significantly greater or less than the solvent control were identified.

Results

SCN Hatching Assay

Nineteen synthetic analogs of monoterpenes significantly affected the hatching of SCN in vitro. Seventeen inhibited hatching by 46% to 96% across both concentrations and times of exposure compared to the solvent control (FIGS. 3A-D). Two compounds stimulated hatching by 287% to 385% relative to the solvent control, but only at 100 ppm with continuous exposure (FIGS. 3A-D).

Compounds Only Tested at 10 ppm

Almost all compounds were tested at 100 ppm, provided they were sufficiently soluble in the solvent system at this concentration. Due to low solubility in water, the following compounds were only tested at 10 ppm: a-bromocinnamaldehyde, JSK1064, JSK1081, JSK2071, and JSK3011.

Egg Hatch Modulation Data

Because of the complexity of the experimental design and the large variation in hatch rates between different testing blocks, as well as the long duration over which testing has occurred, the statistical analysis is not straight-forward. First, within each block $b_i$, the mean μi hatch rate (in percent) in the solvent control is calculated (in blocks with both short-term and continuous exposure, these two testing methods are analyzed independently). For each treatment hatch rate $x_j$ in block $b_i$, a "hatching score" $h_{ij}$ is the calculated as $$h_{i,j} = \sinh^{-1}\frac{x_j}{h_i}.$$

The arcsine transformation is used to account for the fact that calculating the ratio of hatching is subject to non-linear effects. A general linear model is then used to account for additional block effects, and Dunnett's adjustment is used as the multiple comparison procedure to control the familywise error rate, as all treatments are compared to the solvent control. Each block also has a water control, and a zinc sulfate positive control, which ensures that the eggs have sufficient viability. These controls were not used in the calculation of significance other than as controls common to each block in the unbalanced incomplete block design experiment.

In the data set forth in Tables 1-4 below, treatments that were statistically significantly different, or nearly so, from controls are shown. The following symbols are used:

| Symbol | p-value |
|---|---|
| . | 0.1 |
| * | 0.05 |
| ** | 0.01 |
| *** | 0.001 |
| **** | <0.0001 |

The estimate column contains an estimate of the difference in hatch rate modulation between the solvent control and the treatment. This is estimated as a percentage hatch rate of the control. For reliability of the magnitude of the effect, more than one block is needed. Due to the high variation in solvent control hatch rates between blocks, some percentage modulations may fall outside the expected range (e.g., below −100%).

Due to the arctangent/tangent conversions, the standard errors of the mean (column SE) are very rough estimates of the standard error. However, the p value column contains the actual p-values.

While many treatments caused a decrease in egg hatch, some compounds caused a statistically significant stimulation of hatching. The "incr" column denotes whether the significant difference is due to an increase of egg hatching. Compounds that have been tested more than once have the number of blocks listed.

TABLE 1

| Short-Term Exposure Assay, 100 ppm | | | | | | |
|---|---|---|---|---|---|---|
| Treatment | estimate | SE | p.value | symb | incr | blocks |
| 4-OMe-BNS | −117.9 | 15.2 | <0.0001 | **** | | 2 |
| 4-F-BNS | −113.8 | 15.2 | <0.0001 | **** | | 2 |
| 4-M-BNS | −112.8 | 15.2 | <0.0001 | **** | | 2 |
| 4-Br-BNS | −112.2 | 15.2 | <0.0001 | **** | | 2 |
| BM-BNS | −111.3 | 15.2 | <0.0001 | **** | | 2 |
| a-chloro-cinnamaldehyde | −104.9 | 15.3 | <0.0001 | **** | | 2 |
| cinnamaldehyde | −88.4 | 15.3 | <0.0001 | **** | | |
| 4-($Me_2N$)cinnamaldehyde | −82.2 | 15.1 | <0.0001 | **** | | |
| 4-methoxy-cinnamaldehyde | −80.8 | 15.1 | <0.0001 | **** | | 2 |
| JSK3089 | −78.2 | 10.7 | <0.0001 | **** | | 3 |
| BNS | −76.3 | 8.8 | <0.0001 | **** | | 3 |
| methyl styryl ketone | −75.4 | 15.3 | $4^{e-04}$ | *** | | 2 |
| JSK3087 | −68.5 | 8.8 | <0.0001 | **** | | 4 |
| JSK3271 | −60.7 | 15.1 | 0.00816 | ** | | 2 |
| JSK3145 | −58.9 | 8.8 | <0.0001 | **** | | 4 |
| 4-chlorocinnamaldehyde | −54.7 | 10.7 | <0.0001 | **** | | 3 |
| JSK3110 | −53 | 14.9 | 0.03354 | * | | 2 |
| JSK3131 | −46.8 | 10.7 | 0.00169 | ** | | 3 |
| JSK3086 | −45.3 | 10.6 | 0.00248 | ** | | 2 |
| JSK3088 | −41.8 | 10.6 | 0.00813 | ** | | 2 |
| JSK3139 | −41.7 | 10.7 | 0.00873 | ** | | 2 |
| JSK3141 | −32.8 | 10.7 | 0.11288 | | | 2 |

TABLE 1-continued

| Short-Term Exposure Assay, 100 ppm | | | | | | |
|---|---|---|---|---|---|---|
| Treatment | estimate | SE | p.value | symb | incr | blocks |
| abamectin | −31.9 | 10.9 | 0.15475 | | | 2 |
| D-limonene | 35 | 10.9 | 0.07532 | · | + | 2 |
| zinc sulfate | 54.7 | 3.1 | <0.0001 | **** | + | |

TABLE 2

| Short-Term Exposure Assay, 10 ppm | | | | | | |
|---|---|---|---|---|---|---|
| Treatment | estimate | SE | p.value | symb | incr | blocks |
| 4-Br-BNS | −109 | 14.9 | <0.0001 | **** | | 2 |
| 4-M-BNS | −98.8 | 14.9 | <0.0001 | **** | | 2 |
| 4-OMe-BNS | −93.6 | 14.9 | <0.0001 | **** | | 2 |
| 4-F-BNS | −93.1 | 14.9 | <0.0001 | **** | | 2 |
| BNS | −66.4 | 8.7 | <0.0001 | **** | | 3 |
| 4-chloro-cinnamaldehyde | −51.1 | 10.5 | 0.00023 | *** | | 3 |
| JSK3089 | −31.7 | 10.5 | 0.13301 | | | 3 |
| JSK3087 | −26.9 | 8.7 | 0.10398 | | | 4 |
| zinc sulfate | 54.7 | 3.1 | <0.0001 | **** | + | |

TABLE 3

| Continuous Exposure Assay, 100 ppm | | | | | | |
|---|---|---|---|---|---|---|
| Treatment | estimate | SE | p.value | symb | incr | blocks |
| cinnamaldehyde | −95.9 | 14.3 | <0.0001 | **** | | |
| 4-M-BNS | −88.5 | 9.7 | <0.0001 | **** | | 2 |
| methyl styryl ketone | −85 | 8.4 | <0.0001 | **** | | 2 |
| JSK3087 | −80.5 | 6.4 | <0.0001 | **** | | 4 |
| 4-OMe-BNS | −79.9 | 8.3 | <0.0001 | **** | | 2 |
| JSK3089 | −79.6 | 7.1 | <0.0001 | **** | | 3 |
| 4Br-BNS | −76.8 | 8.3 | <0.0001 | **** | | 2 |
| BNS | −76.4 | 8.1 | <0.0001 | **** | | 3 |
| a-chloro-cinnamaldehyde | −75.5 | 8.4 | <0.0001 | **** | | 2 |
| 4-methoxy-cinnamaldehyde | −74.9 | 8.3 | <0.0001 | **** | | 2 |
| JSK1132 | −74.7 | 13.8 | <0.0001 | **** | | |
| JSK4018 | −71.5 | 8 | <0.0001 | **** | | 3 |
| JSK3114 | −71.4 | 8.3 | <0.0001 | **** | | 2 |
| 4-chloro-cinnamaldehyde | −68.5 | 7.2 | <0.0001 | **** | | 3 |
| JSK3271 | −67.6 | 9.9 | <0.0001 | **** | | 2 |
| 4-($Me_2N$)cinnamaldehyde | −66.2 | 14.2 | 0.00106 | ** | | |
| JSK3285 | −63.5 | 8 | <0.0001 | **** | | 3 |
| JSK3141 | −62.2 | 9.9 | <0.0001 | **** | | 2 |
| JSK3091 | −59.7 | 7.1 | <0.0001 | **** | | 3 |
| JSK3135 | −58.5 | 8.1 | <0.0001 | **** | | 3 |
| JSK3209 | −58.4 | 8.1 | <0.0001 | **** | | 3 |
| 4H3MC | −55.3 | 14 | 0.01223 | * | | |
| BM—BNS | −55.1 | 9.8 | <0.0001 | **** | | 2 |
| cinnamonitrile | −53.8 | 14.1 | 0.01858 | | | |
| JSK3088 | −53.3 | 9.9 | <0.0001 | **** | | 2 |
| citral | −52.2 | 14.3 | 0.03247 | * | | |
| abamectin | −51.4 | 10.1 | <0.0001 | **** | | 2 |
| 4-F-BNS | −47.4 | 9.8 | 0.00031 | *** | | 2 |
| JSK3145 | −47 | 6.4 | <0.0001 | **** | | 4 |
| JSK3144 | −46.9 | 9.9 | 0.00047 | *** | | 2 |
| JSK3086 | −45.6 | 9.9 | $7^{e-04}$ | *** | | 2 |
| JSK3169 | −43.5 | 9.8 | 0.00139 | ** | | 2 |
| JSK3090 | −41.3 | 8.1 | <0.0001 | **** | | 3 |
| JSK3139 | −41.3 | 9.9 | 0.00399 | ** | | 2 |
| JSK4012 | −37.9 | 10.6 | 0.03343 | * | | 2 |
| JSK3110 | −32.2 | 9.9 | 0.01771 | * | | 2 |
| JSK3296 | −32.2 | 8 | 0.00689 | ** | | 3 |
| cinnamic acid | −31.5 | 10.2 | 0.13076 | | | 2 |
| JSK3106 | −31.4 | 8.1 | 0.01082 | * | | 3 |
| JSK3131 | −30.6 | 7.1 | 0.00209 | ** | | 3 |

TABLE 3-continued

| Continuous Exposure Assay, 100 ppm | | | | | | |
|---|---|---|---|---|---|---|
| Treatment | estimate | SE | p.value | symb | incr | blocks |
| JSK3297 | −23.7 | 8 | 0.17926 | | | 3 |
| eucalyptol | 30 | 10 | 0.16216 | | | 2 |
| JSK3092 | 37.4 | 7.1 | <0.0001 | **** | | 4 |
| zinc sulfate | 54.9 | 2.9 | <0.0001 | **** | | |

TABLE 4

| Continuous Exposure Assay, 10 ppm | | | | | | |
|---|---|---|---|---|---|---|
| Treatment | estimate | SE | p.value | symb | incr | blocks |
| 4-M-BNS | −108.9 | 15.1 | <0.0001 | **** | | 2 |
| 4-OMe-BNS | −105.7 | 15.1 | <0.0001 | **** | | 2 |
| 4-Br-BNS | −102.3 | 15.1 | <0.0001 | **** | | 2 |
| 4-F-BNS | −98.6 | 15.1 | <0.0001 | **** | | 2 |
| BNS | −72.5 | 8.7 | <0.0001 | **** | | 3 |
| BM-BNS | −63.9 | 15.1 | 0.00453 | ** | | 2 |
| 4-chloro-cinnamaldehyde | −53.7 | 10.6 | $1^{e-04}$ | **** | | 3 |
| zinc sulfate | 54.7 | 3.1 | <0.0001 | **** | + | |

RKN Quick Sand Assay

Figure 4:
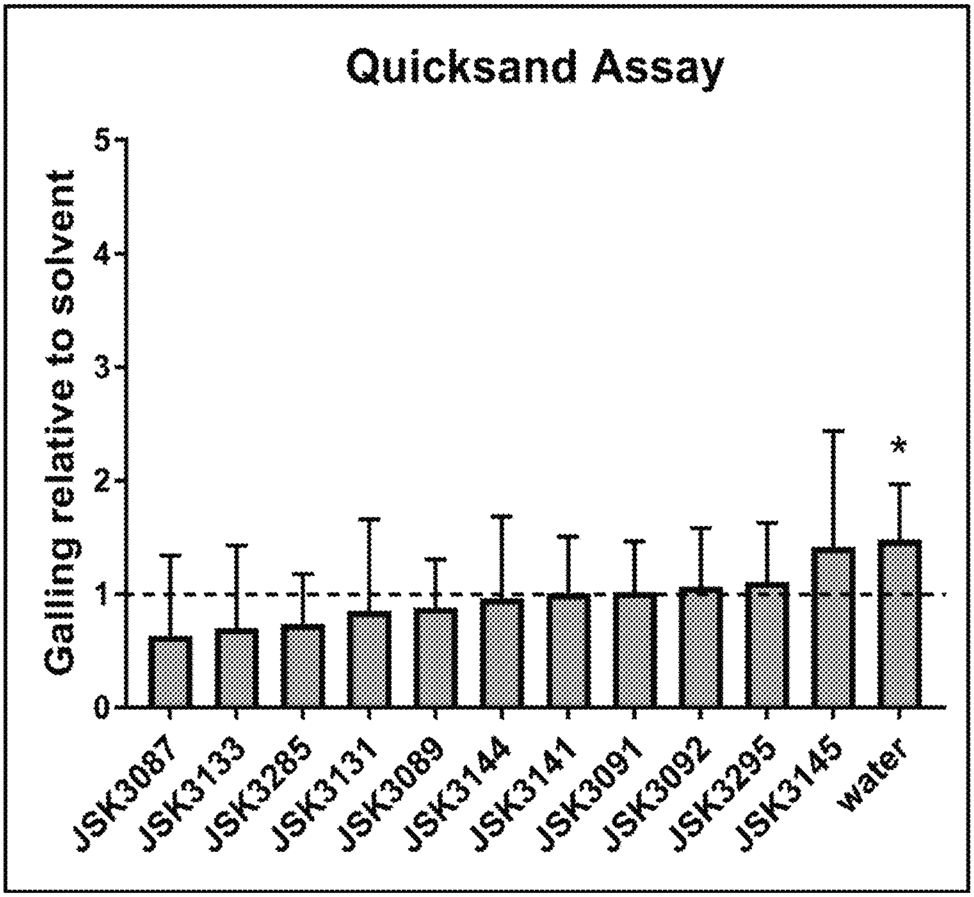
FIG. 4 is a graph showing the effects of synthetic analogs of monoterpenes on gall formation on cucumber roots caused by RKN. * indicates significant difference (alpha=0.05) from the solvent.

The percentage galling for the water, solvent, and abamectin control treatments was 39%, 24%, and 0%, respectively. The galling of plants treated with the monoterpene analogs ranged from 16% to 35%, and none of the tested compounds significantly decreased RKN galling compared to the solvent control (FIG. 4).

Example 3—Microplot Experiment

Materials

Microplots were constructed by inserting 1-m-diameter by 0.25-m-tall circles of plastic drainage pipe into the soil in a field on a university-owned research farm located 10 km (6 miles) due west of Ames, IA. The field was not infested with SCN prior to being infested for the experiment. The inside diameter of each microplot had a surface area of 0.86 $m^2$.

Figure 5A:
FIGS. 5A-H are photographs from a microplot experiment conducted in a field.
Figure 5B:
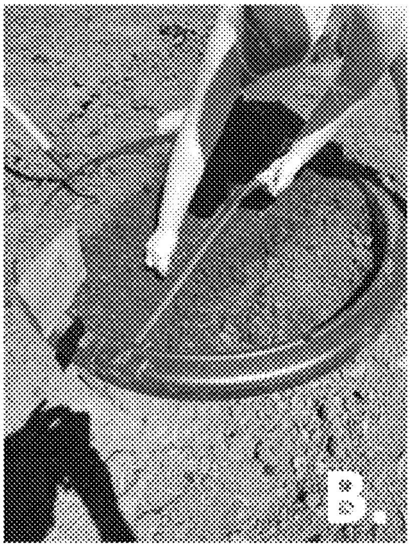
Figure 5C:
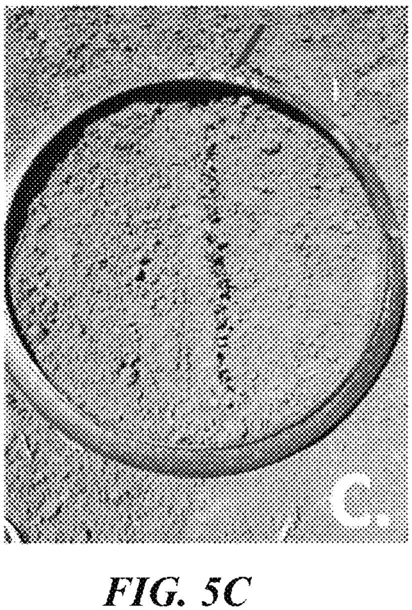
Figure 5D:
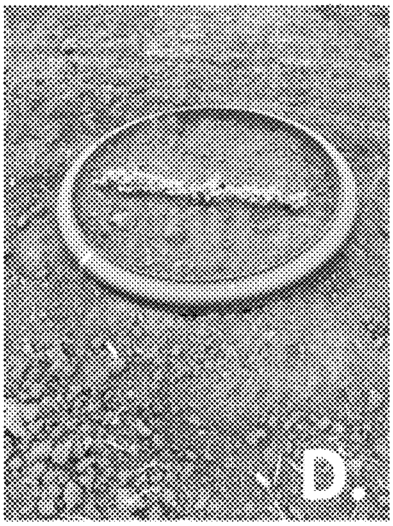
Figure 5E:
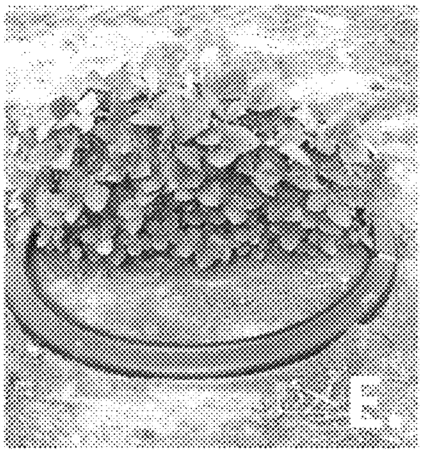
Figure 5F:
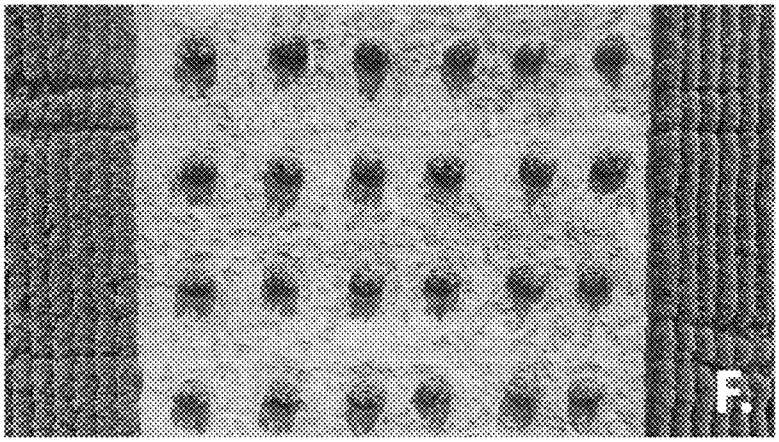
Figure 5G:
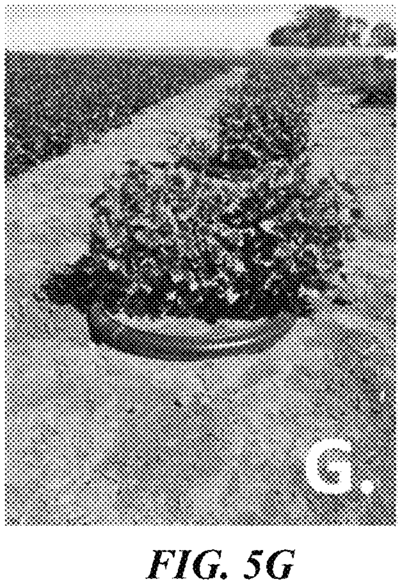
Figure 5H:
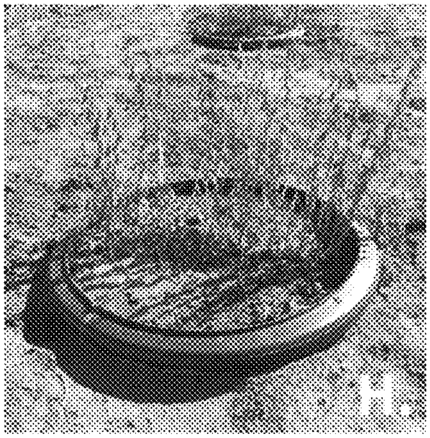

The soil in the top 20 cm of each microplot was loosened, turned over, and artificially infested with approximately 570,000 SCN eggs contained within cysts in 1 liter of soil from greenhouse cultures. The SCN inoculum was applied in a band across the middle of the microplot (FIG. 5A), then 1.65 L of treatment solution were applied over the infested soil. Treatments were 100 ppm solutions of three of the most-promising compounds for effects on SCN, based on results of previous hatching and growth chamber studies. Two different control treatments consisted of microplots receiving 1.65 L of autoclaved, deionized water and microplots receiving 1.65 L of the solvent used to dilute the compounds. The SCN-infested soil inoculum and applied liquid treatment were rototilled into the soil in each microplot, then 40 seeds of the SCN-susceptible variety "Williams 82" were planted in a single, central row within each microplot (FIG. 5B). Similarly, seeds of the SCN-resistant variety "Jack" were planted in microplots infested with SCN inoculum and treated with water as a third control treatment. There were four replications of each of the six treatments arranged in a randomized complete block design. Microplots were spaced 1 m apart in rows separated by 3 m to avoid cross contamination among microplots (FIG. 5F). Plants were grown for the entire 2020 growing season (FIGS. 5C through 5H).

The total number of plants growing in each microplot were counted (i.e., a "stand count") 34 days after planting. A total of five soil cores, 2 cm in diameter and 15 to 20 cm deep, were collected from the root zone on either side of the row of soybean plants in each microplot 34 days after planting, 64 days after planting, and when the plants were removed from the microplots to determine the SCN population densities. SCN requires approximately 30 days to complete a single generation. Soil samples collected at 34 and 64 days after planting coincided approximately with the end of the first and second SCN generations of the growing season, when differences in SCN population densities likely may have been detected due to effects of the treatments on SCN reproduction. SCN cysts (dead females full of eggs) were extracted from the soil samples using a wet sieving method, and eggs were released from the recovered cysts by crushing cysts with a motorized rubber stopper. Recovered eggs were stained with acid fuchsin and counted under a microscope to determine their number per 100 $cm^3$ of soil.

The stems of soybean plants in each microplot were cut at the soil line, and all plants from each microplot were placed in large paper bags and stored in an unheated shed until they were further processed. The dry weight of all plants in each microplot was determined (total plant biomass at harvest), and then all plants from each microplot were fed through a plot combine to collect and weigh the seeds (seed biomass).

Results

The results of the Microplot Experiment are summarized in Table 5 below. There were no significant differences among treatments in stand, indicating that there were no adverse effects of the compounds on seed germination and seedling emergence. There were no significant differences seen among treatments in SCN numbers in the soil 34 days after planting and at harvest. The soil SCN egg population densities 64 days after planting for the beta-nitrostyrene, 4-methyl beta-nitrostyrene, and 4-chloro styryl cyclopropyl ketone treatments were significantly lower than those in the susceptible/water treatment. Overall plant biomass (stems, pods, and seeds combined) for the beta-nitrostyrene treatment was significantly greater than that for the susceptible/water treatment at the end of the season. Seed weights (analogous to grain yield) of the beta-nitrostyrene, 4-methyl beta-nitrostyrene, and 4-chloro styryl cyclopropyl ketone treatments were significantly greater than the susceptible/water treatment.

TABLE 5

Results from the Microplot Experiment

| | | Stand | SCN Population Densities (# eggs per 100 $cm^3$ soil) | | | Biomass at harvest g | |
|---|---|---|---|---|---|---|---|
| Variety | Treatment compound | 34 DAP | 34 DAP | 64 DAP | harvest | total | seed |
| susceptible | beta-nitrostyrene (BNS) | 30.0 | 3,200 | 3,250 | 5,900 | 753 | 363 |
| susceptible | 4-methyl beta-nitrostyrene (4M-BNS) | 30.0 | 5,800 | 7,400 | 9,800 | 654 | 322 |
| susceptible | 4-chloro styryl cyclopropyl ketone (JSK3087) | 27.5 | 7,275 | 4,700 | 6,400 | 668 | 327 |
| susceptible | solvent | 26.0 | 2,725 | 3,750 | 8,150 | 754 | 372 |
| susceptible | water | 27.8 | 4,150 | 12,700 | 11,800 | 586 | 227 |
| resistant | water | 28.0 | 3,600 | 4,275 | 10,150 | 707 | 340 |
| | Mean: | 28.2 | 4,458 | 6,013 | 8,700 | 687 | 326 |
| | ANOVA P value: | 0.2352 | 0.1384 | 0.0007 | 0.4004 | 0.0261 | 0.0014 |
| | LSD (α = 0.10): | — | — | 3,130 | — | 85.5 | 49.9 |

Numbers in the table above are means of four replicate microplots per treatment.
The SCN-susceptible variety used was Williams 82; the resistant variety was Jack.
Stand is the total number of plants per microplot assessed 34 days after planting (DAP).
Least significant difference (LSD) values were not calculated when a significant treatment effect was not detected (P > 0.10) by analysis of variance (ANOVA).

Suppression of SCN numbers 64 days after planting and increases in seed yield occurred in plots with the beta-nitrostyrene (BNS), 4-methyl beta-nitrostyrene (4M-BNS), and 4-chloro styryl cyclopropyl ketone (JSK3087) treatments relative to plots with the susceptible/water treatment. The beta-nitrostyrene treatment also had increased total plant biomass at harvest relative to the susceptible/water treatment.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound selected from

JSK3086

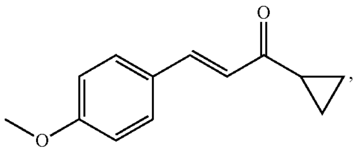

,

JSK3087

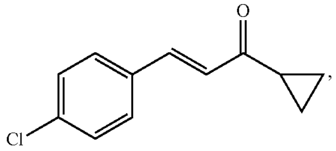

,

JSK3088

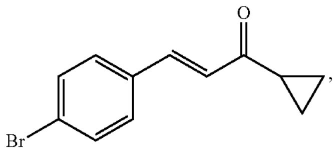

,

-continued
JSK3089
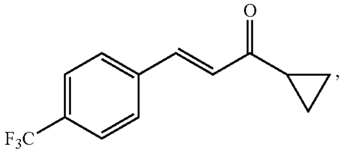
JSK3090
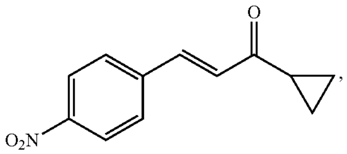
JSK3106
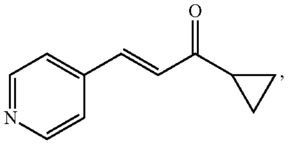
JSK3110
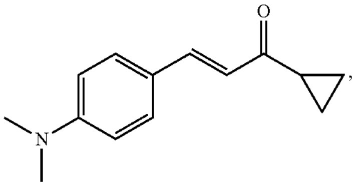
JSK3114
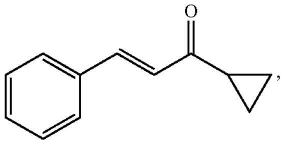
JSK3135
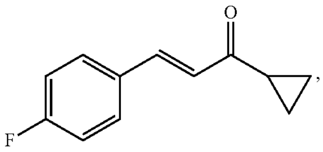
JSK3139
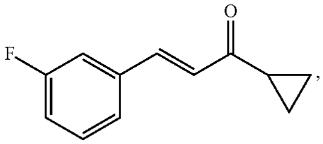
JSK3141
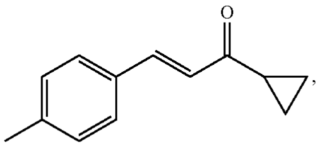
JSK3144
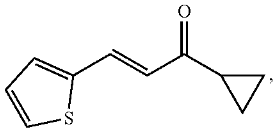
JSK3145
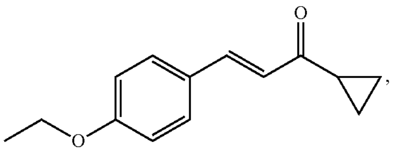
-continued
JSK3285
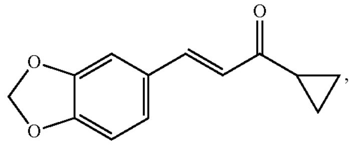
JSK3295
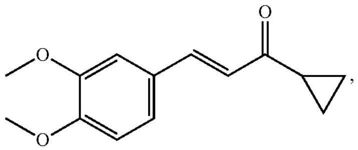
JSK4012
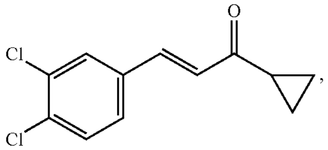
JSK3091
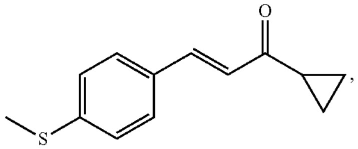
JSK3142
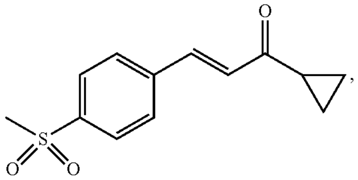
JSK3169
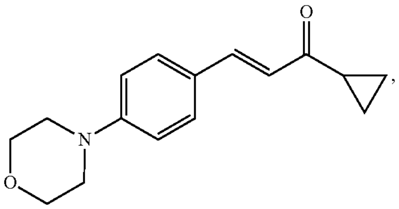
JSK3209
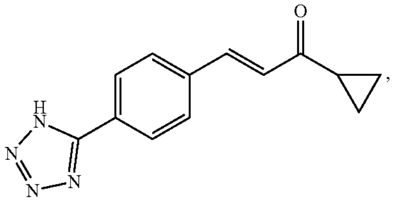
JSK3294
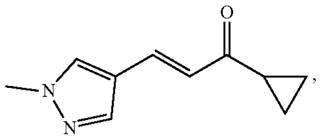
JSK3296
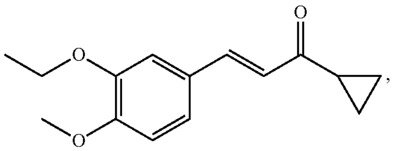

-continued
JSK3297
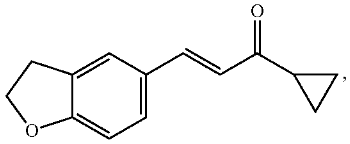
, and
JSK4018
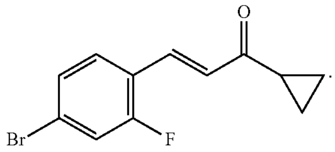
.
2. A composition comprising:
a compound of claim 1 and
an agriculturally acceptable carrier.
* * * * *